US012419971B2

(12) United States Patent
Fafournoux et al.

(10) Patent No.: US 12,419,971 B2
(45) Date of Patent: Sep. 23, 2025

(54) DIET CONTROLLED EXPRESSION OF A NUCLEIC ACID ENCODING A PRO-APOPTOTIC PROTEIN

(71) Applicants: INSTITUT NATIONAL DE RECHERCHE POUR L'AGRICULTURE, L'ALIMENTATION ET L'ENVIRONNEMENT, Paris (FR); CENTRE NATIONAL DE LA RECHERCHE SCIENTIFIQUE, Paris (FR); SORBONNE UNIVERSITE, Paris (FR); ASSISTANCE PUBLIQUE-HÔPITAUX DE PARIS, Paris (FR); INSTITUT NATIONAL DE LA SANTE ET DE LA RECHERCHE MEDICALE (INSERM), Paris (FR); INSTITUT DU CERVEAU ET DE LA MOELLE EPINIERE, Paris (FR)

(72) Inventors: Pierre Fafournoux, Auriers (FR); Jacques Mallet, Paris (FR)

(73) Assignees: INSTITUT NATIONAL DE RECHERCHE POUR L'AGRICULTURE, L'ALIMENTATION L'ENVIRONNEMENT, Paris (FR); CENTRE NATIONAL DE LA RECHERCHE SCIENTIFIQUE, Paris (FR); SORBONNE UNIVERSITE, Paris (FR); ASSISTANCE PUBLIQUE-HÔPITAUX DE PARIS, Paris (FR); INSTITUT NATIONAL DE LA SANTE ET DE LA RECHERCHE MEDICALE (INSERM), Paris (FR); INSTITUT DU CERVEAU ET DE LA MOELLE EPINIERE, Paris (FR)

( * ) Notice: Subject to any disclaimer, the term of this patent is extended or adjusted under 35 U.S.C. 154(b) by 849 days.

(21) Appl. No.: 16/727,647

(22) Filed: Dec. 26, 2019

(65) Prior Publication Data
US 2020/0188533 A1 Jun. 18, 2020

Related U.S. Application Data

(62) Division of application No. 16/306,832, filed as application No. PCT/EP2017/063422 on Jun. 2, 2017, now abandoned.

(60) Provisional application No. 62/345,162, filed on Jun. 3, 2016.

(51) Int. Cl.
A61K 48/00 (2006.01)
A01K 67/0275 (2024.01)
A61K 35/00 (2006.01)
A61K 45/06 (2006.01)
C07K 14/705 (2006.01)
C12Q 1/6897 (2018.01)

(52) U.S. Cl.
CPC ...... A61K 48/0058 (2013.01); A01K 67/0275 (2013.01); A61K 35/00 (2013.01); A61K 45/06 (2013.01); C07K 14/70575 (2013.01); C12Q 1/6897 (2013.01); A01K 2207/25 (2013.01); A01K 2217/30 (2013.01); A01K 2227/105 (2013.01); A01K 2267/0331 (2013.01); A01K 2267/0393 (2013.01); C12N 2740/16043 (2013.01); C12N 2830/30 (2013.01)

(58) Field of Classification Search
CPC .................................................. A61K 48/0058
See application file for complete search history.

(56) References Cited

U.S. PATENT DOCUMENTS

2014/0322184 A1* 10/2014 Farfournoux ........ A61K 48/005
424/93.21

OTHER PUBLICATIONS

Marin et al. (Human Gene Therapy Methods 23:376-386 (Dec. 2012)). (Year: 2012).*
Waehler et al. (Nature Reviews Genetics vol. 8, pp. 573-587 (2007)) (Year: 2007).*
Greco et al. (Frontiers in Pharmacology. May 2015; 6(95): 1-13) (Year: 2015).*
Traversari et al., "The potential immunogenicity of the TK suicide gene does not prevent full clinical benefit associated with the use of TK-transduced donor lymphocytes in HSCT for hematologic malignancies". Blood. Jun. 1, 2007;109(11):47 (Year: 2007).*
Jones et al. "Improving the safety of cell therapy products by suicide gene transfer". Front Pharmacol. Nov. 27, 2014; 5:254. (Year: 2014).*
May 14, 2021 U.S Office Action issued U.S. Appl. No. 16/306,832.
Waxman et al. (Cancer Research 63, 8563-8572, Dec. 15, 2003]). (Year: 2003).
Oct. 7, 2021 Office Action issued in U.S. Appl. No. 16/306,832.

(Continued)

Primary Examiner — Allison M Fox
Assistant Examiner — Hanan Isam Abuzeineh
(74) Attorney, Agent, or Firm — Oliff PLC

(57) ABSTRACT

A nucleic acid for the controlled expression of a nucleic acid encoding a pro-apoptotic protein in an individual, including: a regulatory polynucleotide including a minimal promoter and at least one AARE (amino acid response element) nucleic acid, the regulatory polynucleotide being activated in an individual upon consumption of a diet deficient in at least one essential amino acid; and a nucleic acid encoding a pro-apoptotic protein, which is placed under the control of the regulatory polynucleotide.

Figure 1:
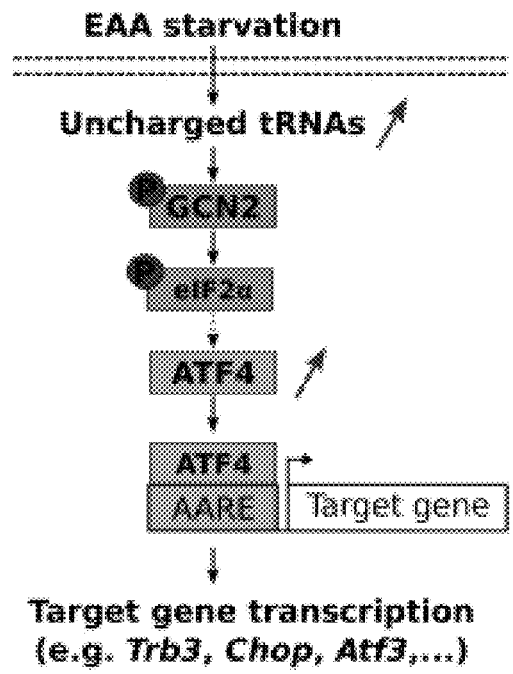

10 Claims, 10 Drawing Sheets
Specification includes a Sequence Listing.

(56) References Cited

OTHER PUBLICATIONS

Chaveroux et al., "In vivo imaging of the spatiotemporal activity of the eIF2a-ATF4 signaling pathway: Insights into stress and related disorders," Stress Signaling, Apr. 23, 2015, vol. 8, No. 374, pp. 1-11.
Kilberg et al., "ATF4-dependent transcription mediates signaling of amino acid limitation," Trends in Endocrinology and Metabolism, 2009, vol. 20, No. 9, ,pp. 436-443.
Averous et al., "Amino acid deprivation regulates the stress-inducible gene p8 via the GCN2/ATF4 pathway," Biochemical and Biophysical Research Communications, 2011, vol. 413, pp. 24-29.
Bruhat et al., "Amino Acids Control Mammalian Gene Transcription: Activating Transcription Factor 2 is Essential for the Amino Acid Responsiveness of the CHOP Promoter," Mol. Cell. Biol., Oct. 2000, vol. 20, No. 19, pp. 7192-7204.
Bruhat et al., "Amino acids as regulators of gene expression in mammals: Molecular mechanisms," BioFactors, pp. 249-257.
Aug. 22, 2017 International Search Report issued in International Patent Application No. PCT/EP2017/063422.

\* cited by examiner

SEQUENCE LISTING

<160> NUMBER OF SEQ ID NOS: 8

<210> SEQ ID NO 1
<211> LENGTH: 16
<212> TYPE: DNA
<213> ORGANISM: Artificial Sequence
<220> FEATURE:
<223> OTHER INFORMATION: AARE sequence from the TRIB3 gene

<400> SEQUENCE: 1
cggtttgcat cacccg     16

<210> SEQ ID NO 2
<211> LENGTH: 16
<212> TYPE: DNA
<213> ORGANISM: Artificial Sequence
<220> FEATURE:
<223> OTHER INFORMATION: AARE sequence from the CHOP gene

<400> SEQUENCE: 2
aacattgcat catccc     16

<210> SEQ ID NO 3
<211> LENGTH: 16
<212> TYPE: DNA
<213> ORGANISM: Artificial Sequence

```
<220> FEATURE:
<223> OTHER INFORMATION: AARE sequence from the ASNS gene

<400> SEQUENCE: 3
gaagtttcat catgcc                                                    16

<210> SEQ ID NO 4
<211> LENGTH: 16
<212> TYPE: DNA
<213> ORGANISM: Artificial Sequence
<220> FEATURE:
<223> OTHER INFORMATION: AARE sequence from the ATF3 gene

<400> SEQUENCE: 4
agcgttgcat cacccc                                                    16

<210> SEQ ID NO 5
<211> LENGTH: 16
<212> TYPE: DNA
<213> ORGANISM: Artificial Sequence
<220> FEATURE:
<223> OTHER INFORMATION: AARE sequence from the SNAT2 gene

<400> SEQUENCE: 5
gatattgcat cagttt                                                    16

<210> SEQ ID NO 6
<211> LENGTH: 317
<212> TYPE: DNA
<213> ORGANISM: Artificial Sequence
<220> FEATURE:
<223> OTHER INFORMATION: Regulatory polypeptide comprising the Thymidine
      kinase (Tk) minimal promoter and six copies of the AARE nucleic
      acid sequence from the TRIB3 gene

<400> SEQUENCE: 6
ggtaccgatt agctccggtt tgcatcaccc ggaccggggg attagctccg gtttgcatca     60
cccggaccgg gggattagct ccggtttgca tcacccggac cggggccgg gcgcgtgcta    120 gcgattagct ccggtttgca tcacccggac cgggggatta gctccggttt gcatcacccg    180
gaccggggga ttagctccgg tttgcatcac ccggaccggg gactcgaggt ccacttcgca    240
tattaaggtg acgcgtgtgg cctcgaacac cgagcgaccc tgcagcgacc cgcttaacag    300
cgtcaacagc gtgccgc                                                  317

<210> SEQ ID NO 7
<211> LENGTH: 864
<212> TYPE: DNA
<213> ORGANISM: Artificial Sequence
<220> FEATURE:
<223> OTHER INFORMATION: cDNA of TRAIL protein

<400> SEQUENCE: 7
atggctatga tggaggtcca gggggggaccc agcctgggac agacctgcgt gctgatcgtg     60
atcttcacag tgctcctgca gtctctctgt gtggctgtaa cttacgtgta ctttaccaac    120
gagctgaagc agatgcagga caagtactcc aaaagtggca ttgcttgttt cttaaaagaa    180
gatgacagtt attgggaccc caatgacgaa gagagtatga cagcccctg ctggcaagtc    240 aagtggcaac tccgtcagct cgttagaaag atgatttga gaacctctga ggaaaccatt    300
tctacagttc aagaaaagca acaaaatatt tctcccctag tgagagaaag aggtcctcag    360
agagtagcag ctcacataac tgggaccaga ggaagaagca acacattgtc ttctccaaac    420
```

| | |
|---|---|
| tccaagaatg aaaaggctct gggccgcaaa ataaactcct gggaatcatc aaggagtggg | 480 |
| cattcattcc tgagcaactt gcacttgagg aatggtgaac tggtcatcca tgaaaaaggg | 540 |
| ttttactaca tctattccca acatactttc gatttcagg aggaaataaa agaaaacaca | 600 |
| aagaacgaca aacaaatggt ccaatatatt tacaaataca caagttatcc tgaccctata | 660 |
| ttgttgatga aaagtgctag aaatagttgt tggtctaaag atgcagaata tggactctat | 720 |
| tccatctatc aagggggaat atttgagctt aaggaaaatg acagaatttt tgtttctgta | 780 |
| acaaatgagc acttgataga catggaccat gaagccagtt ttttttggggc cttttagtt | 840 |
| ggctaaaccg gtgctagctc taga | 864 |

<210> SEQ ID NO 8
<211> LENGTH: 3806
<212> TYPE: DNA
<213> ORGANISM: Artificial Sequence
<220> FEATURE:
<223> OTHER INFORMATION: Plasmid pENTR comprising six copies of the AARE
      nucleic acid from Trib3 gene sequence, Tk minimal promoter and the
      cDNA encoding for TRAIL protein

<400> SEQUENCE: 8

| | |
|---|---|
| caccggtacc gattagctcc ggtttgcatc acccggaccg ggggattagc tccggtttgc | 60 |
| atcacccgga ccgggggatt agctccggtt tgcatcaccc ggaccggggg ccgggcgcgt | 120 |
| gctagcgatt agctccggtt tgcatcaccc ggaccggggg attagctccg gtttgcatca | 180 |
| cccggaccgg gggattagct ccggtttgca tcacccggac cggggactcg aggtccactt | 240 |
| cgcatattaa ggtgacgcgt gtggcctcga acaccgagcg accctgcagc gacccgctta | 300 |
| acagcgtcaa cagcgtgccg caagcttgaa ttctgatcag cattccggta ctgttggaaa | 360 |
| gccaccatgg ctatgatgga ggtccagggg gacccagcc tgggacagac ctgcgtgctg | 420 |
| atcgtgatct tcacagtgct cctgcagtct ctctgtgtgg ctgtaactta cgtgtacttt | 480 |
| accaacgagc tgaagcagat gcaggacaag tactccaaaa gtggcattgc ttgtttctta | 540 |
| aagaagatg acagttattg ggaccccaat gacgaagaga gtatgaacag cccctgctgg | 600 |
| caagtcaagt ggcaactccg tcagctcgtt agaaagatga ttttgagaac ctctgaggaa | 660 |
| accatttcta cagttcaaga aaagcaacaa atatttctc ccctagtgag agaaagaggt | 720 |
| cctcagagag tagcagctca cataactggg accagaggaa gaagcaacac attgtcttct | 780 |
| ccaaactcca agaatgaaaa ggctctgggc cgcaaaataa actcctggga atcatcaagg | 840 |
| agtgggcatt cattcctgag caacttgcac ttgaggaatg gtgaactggt catccatgaa | 900 |
| aaagggtttt actacatcta ttcccaaaca tactttcgat tcaggagga aataaaagaa | 960 |
| aacacaaaga cgacaaaca atggtccaa tatatttaca aatacacaag ttatcctgac | 1020 |
| cctatattgt tgatgaaaag tgctagaaat agttgttggt ctaaagatgc agaatatgga | 1080 |
| ctctattcca tctatcaagg gggaatattt gagcttaagg aaaatgacag aatttttgtt | 1140 |
| tctgtaacaa atgagcactt gatagacatg gaccatgaag ccagttttt tggggccttt | 1200 |
| ttagttggct aaaccggtgc tagctctaga agggtgggc gcgccgaccc agctttcttg | 1260 |
| tacaaagttg gcattataag aaagcattgc ttatcaattt gttgcaacga acaggtcact | 1320 |
| atcagtcaaa ataaaatcat tatttgccat ccagctgata tcccctatag tgagtcgtat | 1380 |
| tacatggtca tagctgtttc ctggcagctc tggcccgtgt ctcaaaatct ctgatgttac | 1440 |
| attgcacaag ataaaaatat atcatcatga acaataaaac tgtctgctta cataaacagt | 1500 |
| aatacaaggg gtgttatgag ccatattcaa cgggaaacgt cgaggccgcg attaaattcc | 1560 |

-continued

```
aacatggatg ctgatttata tgggtataaa tgggctcgcg ataatgtcgg gcaatcaggt    1620
gcgacaatct atcgcttgta tgggaagccc gatgcgccag agttgtttct gaaacatggc    1680
aaaggtagcg ttgccaatga tgttacagat gagatggtca gactaaactg gctgacggaa    1740
tttatgcctc ttccgaccat caagcatttt atccgtactc ctgatgatgc atggttactc    1800
accactgcga tccccggaaa aacagcattc caggtattag aagaatatcc tgattcaggt    1860
gaaaatattg ttgatgcgct ggcagtgttc ctgcgccggt tgcattcgat tcctgtttgt    1920
aattgtcctt ttaacagcga tcgcgtattt cgtctcgctc aggcgcaatc acgaatgaat    1980
aacggtttgg ttgatgcgag tgattttgat gacgagcgta atggctggcc tgttgaacaa    2040
gtctggaaag aaatgcataa acttttgcca ttctcaccgg attcagtcgt cactcatggt    2100
gatttctcac ttgataacct tattttgac gaggggaaat taataggttg tattgatgtt    2160
ggacgagtcg gaatcgcaga ccgataccag gatcttgcca tcctatggaa ctgcctcggt    2220
gagttttctc cttcattaca gaaacggctt tttcaaaaat atggtattga taatcctgat    2280
atgaataaat tgcagtttca tttgatgctc gatgagtttt tctaatcaga attggttaat    2340
tggttgtaac actggcagag cattacgctg acttgacggg acggcgcaag ctcatgacca    2400
aaatccctta acgtgagtta cgcgtcgttc cactgagcgt cagaccccgt agaaaagatc    2460
aaaggatctt cttgagatcc ttttttttctg cgcgtaatct gctgcttgca acaaaaaaa    2520
ccaccgctac cagcggtggt ttgtttgccg gatcaagagc taccaactct ttttccgaag    2580
gtaactggct tcagcagagc gcagatacca aatactgtcc ttctagtgta gccgtagtta    2640
ggccaccact tcaagaactc tgtagcaccg cctacatacc tcgctctgct aatcctgtta    2700
ccagtggctg ctgccagtgg cgataagtcg tgtcttaccg ggttggactc aagacgatag    2760
ttaccggata aggcgcagcg gtcgggctga acggggggtt cgtgcacaca gcccagcttg    2820
gagcgaacga cctacaccga actgagatac ctacagcgtg agcattgaga aagcgccacg    2880
cttcccgaag ggagaaaggc ggacaggtat ccggtaagcg gcagggtcgg aacaggagag    2940
cgcacgaggg agcttccagg gggaaacgcc tggtatcttt atagtcctgt cgggtttcgc    3000
cacctctgac ttgagcgtcg atttttgtga tgctcgtcag ggggggcggag cctatggaaa    3060
aacgccagca acgcggcctt tttacggttc ctggcctttt gctggccttt tgctcacatg    3120
ttctttcctg cgttatcccc tgattctgtg gataaccgta ttaccgcctt tgagtgagct    3180
gataccgctc gccgcagccg aacgaccgag cgcagcgagt cagtgagcga ggaagcggaa    3240
gagcgcccaa tacgcaaacc gcctctcccc gcgcgttggc cgattcatta atgcagctgg    3300
cacgacaggt ttcccgactg gaaagcgggc agtgagcgca acgcaattaa tacgcgtacc    3360
gctagccagg aagagtttgt agaaacgcaa aaggccatc cgtcaggatg gccttctgct    3420
tagtttgatg cctggcagtt tatggcgggc gtcctgcccg ccaccctccg ggccgttgct    3480
tcacaacgtt caaatccgct cccggcggat tgtcctact caggagagcg ttcaccgaca    3540
aacaacagat aaaacgaaag gcccagtctt ccgactgagc ctttcgtttt atttgatgcc    3600
tggcagttcc ctactctcgc gttaacgcta gcatggatgt tttcccagtc acgacgttgt    3660
aaaacgacgg ccagtcttaa gctcgggccc caaataatga ttttattttg actgatagtg    3720
acctgttcgt tgcaacaaat tgatgagcaa tgcttttta taatgccaac tttgtacaaa    3780
aaagcaggct ccgcggccgc ccccctt                                        3806
```

DIET CONTROLLED EXPRESSION OF A NUCLEIC ACID ENCODING A PRO-APOPTOTIC PROTEIN

This is a Division of application Ser. No. 16/306,832 filed Dec. 3, 2018, which in turn is a National Phase Application of PCT/EP2017/063422 filed Jun. 2, 2017, which claims the benefit of U.S. Provisional Application No. 62/345,162 filed Jun. 3, 2016. The disclosure of the prior applications is hereby incorporated by reference herein in its entirety.

FIELD OF THE INVENTION

The present invention relates to a nucleic acid for the controlled expression of a nucleic acid encoding a pro-apoptotic protein in an individual.

In particular, the expression of the nucleic acid may be controlled upon consumption of a diet deficient in at least one essential amino acid.

BACKGROUND OF THE INVENTION

Recently, technological improvements in gene transfer vectors and the development of adequate gene delivery systems have led to substantial clinical successes in gene therapy. However, several barriers must be overcome before gene therapy becomes a widely accepted treatment for a broad group of diseases. Besides safety concerns with respect to available vector systems (e.g. genotoxicity, immune response), the major limitation is the current inability to exogenously modulate the expression of transgenes in a reliable, highly specific, simple and safe manner. One strategy would be to regulate gene expression in a dose-dependent way, for example, by the means of an orally available well-tolerated inducer. In addition, both induction and repression of the gene expression should be reversible.

The scientific community agrees on the fact that cellular therapies could play a role in cancer treatment and regenerative medicine if it were possible to quickly eliminate the infused cells in case of adverse events. More specifically, a fully secured molecular switch would be urgently needed for the adoptive chimeric antigen receptor (CAR) T-cell based treatment to fulfil its great promise in providing a cure for numerous types of cancers. Such a switch would also be invaluable to secure the potential of stem cells-based, in particular hematopoietic stem cells, and iPS cells-based therapies and promote the field of regenerative medicine.

Adoptive T cell therapy initially involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells recognition of tumor specific antigens, and cancer cells destruction. In other words, such a therapy involves manipulating patients' own immune cells to recognize and attack their tumors.

There are several forms of adoptive T cell therapy being used for cancer treatment: culturing and expanding tumor infiltrating lymphocytes (TIL), isolating and expanding one particular T cell clone, as well as using T cells that have been engineered to express a chimeric antigen receptor (CAR) to potently recognize tumor antigens and destroy tumor cells. CAR T-cells have shown the most promise in clinical trials, with over 50 CAR clinical trials currently registered in the US alone (clinicaltrials.gov). Remarkably, chimeric antigen receptor (CAR)-redirected T-cells have given rise to long-term durable remissions and remarkable objective response rates in patients with refractory leukemia.

To date, CAR technology is administered through the custom-made manufacturing of therapeutic products from each patient's own T-cells. However, this patient-specific autologous paradigm is a significant limiting factor in the large-scale deployment of CAR technology. Platforms are presently being developed for the production of "off-the-shelf" CAR T-cells from unrelated third-party donor T-cells in the context of allo-transplantations.

Although CAR T-cells have shown great initial promise in the clinic, these developments has been accompanied by some severe and even fatal side-effects (Gargett and Brown, Front Pharmacol., 2014 Oct. 28; 5:235).

It has been observed that donor T-cell infusion in patients with post-transplant relapse can bring about disease remission through a graft-versus-leukemia effect but this is generally associated with the development of GVHD (graft versus host disease) as a result of alloimmunity against non-hematopoietic tissues (Kolb, Blood, 2008 Dec. 1; 112 (12):4371-83).

On-target but off-tumor adverse effects may occurs because T cells, targeting differentiation antigens, can be expected to also recognize nonmalignant cells that express the same antigens, resulting in adverse events. For example, melanoma patients treated with T cells targeting melanocyte differentiation antigens, such as MART-1 and gp100, often developed vitiligo and uveitis (Teulings et al., 2014; Pigment Cell Melanoma Res. 2014 November; 27(6):1086-96.)

On-target but off-tumor toxicities can be immediately life threatening. A patient with colorectal cancer with lung and liver metastases developed respiratory distress within 15 min of HER2-specific CAR T-cell infusion and subsequently died from multi-organ failure 5 days later.

In each of these cases, the adverse effects occurred despite relatively low levels of antigen expression in the off-tumor sites, thus highlighting the potential for harm in using redirected T cells with high avidity and potency.

As T-cell therapy becomes more effective, acute toxicities have also become more evident and may give rise to the Cytokine release syndrome, which is characterized by fevers, rigors, hypotension and hypoxia. This syndrome has been observed in a number of CD19 CAR T-cell studies as a result of large-scale T-cell activation upon the recognition of CD19+ malignant cells.

One of the attractions of T-cell therapy is the potential for the transferred cells to persist and expand, thus mediating sustained therapeutic effects. However, any adverse effects will also be similarly sustained, can worsen as the cells proliferate, and be associated with cell proliferation, (Tey, Clin Transl Immunology, 2014 Jun. 20; 3(6):e17).

As acknowledged by Zhou et al. "Although cellular therapies may be effective in cancer treatment, their potential for expansion, damage of normal organs, and malignant transformation is a source of concern. The ability to conditionally eliminate aberrant cells in vivo would ameliorate these concerns and broaden the application of cellular therapy" (Methods Mol Biol. 2015; 1317:87-105).

Thus, to fulfill its potential, the adoptive cell transfer technology needs to incorporate a "suicide" safety component, particularly at the level of the CAR T-cells. As will be discussed below, some approaches have been developed but none fully meets the requirements to be safely translated in the clinical setting.

The potential of ESC cells has been largely demonstrated in the context of diseases of the hematopoietic system. Similarly, induced pluripotent stem cell (iPSC) technologies hold great promise for regenerative medicine, based on their unlimited self-renewal capabilities and ability to differentiate to cell types derived from all three embryonic germ layers. Clearly, iPSC-based therapies offer a promising path for patient-specific regenerative medicine.

Assawachananont et al. recently showed that mouse embryonic stem cell- or induced pluripotent stem cell-derived 3D retinal tissue developed a structured outer nuclear layer (ONL) with complete inner and outer segments even in an advanced retinal degeneration model (rd1) that lacked ONL. Host-graft synaptic connections were observed by immunohistochemistry, providing a "proof of concept" for retinal sheet transplantation therapy for advanced retinal degenerative diseases. (Stem Cell Reports. 2014 Apr. 24; 2(5):662-74).

These results, together with work in non-human primate, led the authors above, to undertake the implantation of autologous iPSCs-derived retinal pigment epithelial (RPE) cell sheet into human. This clinical trial was hailed as being the first historical transplant of iPS cell-based product.

The patient had a series of 18 anti-vascular endothelial growth factor (VEGF) ocular injections for both eyes to cope with the constant recurrence of the disease. After the removal of the sub-retinal fibrotic tissue and implantation of the iPS-cell-derived RPE cell sheet, the patient experienced no recurrence of neovascularization at the 6 month point and was free from frequent anti-VEGF injections. Her visual acuity was stabilized and there have been no safety related concerns, at least in September 2015, nearly one year after the transplant.

However, concerns were raised about this trial: "Still, tissues made from iPS cells carry their own concerns, and that had stopped any country from approving them for clinical trial. The body's immune system could attack them, or they might contain some cells that are still in the pluripotent state and cause cancerous growths" (Jeanne Loring, Scripps Research Institute in La Jolla, California).

Clearly, there is a crucial need to equip the iPS cells that are engaged in the production of RPE sheets with a robust built-in safety system. As highlighted above in the context of CAR T-cells infusion, clinical trials (and thereafter treatment) with RPE cells possessing such a system would be considerably safer. Such a safety device would also considerably hasten the emergence of a cure not only for diseases of the eye, but would innervate the entire field of regenerative medicine.

Indeed, existing "suicide" systems have their caveats.

The first suicide gene to have been clinically tested is the herpes simplex virus thymidine kinase (HSVtk) that mediates the conversion of ganciclovir to ganciclovir triphosphate, which is toxic to dividing cells. However, HSVtk as a safety switch has a number of drawbacks, such as the fact that activation of HSV-TK by ganciclovir is relatively slow, requiring 3 days to have a complete effect in vitro (Marin et al., Hum Gene Ther Methods. 2012 December; 23(6):376-86).

Most importantly, the viral TK gene product has intrinsic immunogenicity that may cause transduced cells to be rejected by the host immune system in immunocompetent individuals (Berger et al., Blood. 2006 Mar. 15; 107(6): 2294-302). Additionally, if ganciclovir is used to treat CMV infections in immunocompromised recipients of hemopoietic stem transplants, the use of this suicide gene would result in the unwanted deletion of transduced cells (Bonini et al., Mol Ther. 2007 July; 15(7):1248-52).

An alternative suicide gene system consists of an inducible caspase 9 (iCasp9) gene together with the small-molecule, bio-inert, chemical induction of dimerization (CID) drug, AP1903. The iCasp9 gene contains the intracellular portion of the human caspase 9 protein, a pro-apoptotic molecule, fused to a drug-binding domain derived from human FK506-binding protein (Straathof et al., Blood. 2005 Jun. 1; 105(11):4247-54). Intravenous administration of AP1903 produces cross-linking of the drug-binding domains of this chimeric protein, which in turn dimerizes caspase9 and activates the downstream executioner caspase 3 molecule, resulting in cellular apoptosis.

In an early in vivo experiment using a SCID mouse-human xenograft model, a single dose killed over 99% of circulating human GFP+ T cells by day 3. Importantly, killing via iCasp9 has been found to be extremely rapid with early apoptotic Annexin V+ cells appearing within 30 min, and a complete effect observed by 24 h of CID treatment in vitro (Marin et al., 2012).

Concerning hematopoietic Stem and progenitor cells (Stem Cells. 2015 January; 33(1):91-100), Cyntia Dunbar (NIH) reported that "following stable engraftment of iCasp9 expressing hematopoietic cells in rhesus macaques, administration of AP1903, a chemical inducer of dimerization able to activate iCasp9, specifically eliminated vector-containing cells in all hematopoietic lineages long-term, suggesting activity at the HSPC level. Between 75-94% of vector-containing cells were eliminated by well-tolerated AP1903 dosing, but lack of complete ablation was linked to lower iCasp9 expression in residual cells. Further investigation of resistance mechanisms demonstrated upregulation of Bcl-2 in hematopoietic cell lines transduced with the vector and resistant to AP1903 ablation. These results demonstrate both the potential and the limitations of safety approaches utilizing iCasp9 to HSPC-targeted gene therapy settings, in a model with great relevance to clinical development."

Although the present efficacy of the iCasp9 suicide system might be suitable in some particular situations, it would not adequately overcome a process of tumorigenesis.

In any case, the main issue is that of its inherent immunogenicity.

The team of Malcom Brenner promoted the iCasp9 suicide system. The human origin of the iCasp9 suicide gene probably makes it less immunogenic than suicide genes from xenogeneic sources. There was found no evidence of an immune response against transgenic cells, which persisted at stable levels over the long-term in our patients, but it cannot be ruled out immunogenicity of any component of the construct in other clinical settings (Di Stasi et al.; N. Engl. J. Med. 2011 Nov. 3; 365(18):1673-83).

In essence, the iCasp9 protein is potentially immunogenic because of the synthetic 20-amino-acid peptide and the hinges between this peptide and the two peptide-moieties are of non-human origin. Although no adverse event was observed in an initial clinical trial, which only included a small cohort of patients there is no guaranty that immunological events will not occurs when a larger number of patients will be enrolled, nor will there even be a guaranty.

Clearly, novel suicide systems are needed.

Several nutrition-related studies have been focusing on identifying the role of amino acids (AA) in the regulation of physiological functions, particularly with respect to the mechanisms involved in the regulation of gene expression by AA. After eating a diet deficient in one essential amino acid (EAA), the blood concentration of the limiting EAA decreases rapidly and greatly, triggering an ubiquitous adaptive process referred to as the amino-acid response pathway. The initial step of this pathway is the activation by uncharged tRNA of the mammalian GCN2 protein kinase, which phosphorylates the α subunit of eukaryotic initiation factor 2 (eIF2α) on serine 51, leading to up-regulation of the translation of the activating transcription factor (ATF4). Once induced, ATF4 activates transcription of specific target genes through binding to the Amino Acid Response Element (AARE). The GCN2-eIF2α-ATF4 pathway can be rapidly turned off by the administration of the missing EAA.

Taking advantage of these observations, the patent application WO 2013/068096 disclosed an expression cassette including a gene of interest under the control of an inducible promoter, which includes at least one AARE regulatory sequence and a minimal promoter.

SUMMARY OF THE INVENTION

In a first aspect, the present invention relates to a nucleic acid for the controlled expression of a nucleic acid encoding a pro-apoptotic protein in an individual, comprising:
- a regulatory polynucleotide comprising a minimal promoter and at least one AARE (amino acid response element) nucleic acid, said regulatory polynucleotide being activated in an individual upon consumption of a diet deficient in at least one essential amino acid; and
- a nucleic acid encoding a pro-apoptotic protein, which is placed under the control of the said regulatory polynucleotide.

In a further aspect, the present invention relates to a nucleic acid vector for the controlled expression of a nucleic acid encoding a pro-apoptotic protein, comprising a nucleic acid for the controlled expression of a nucleic acid encoding a pro-apoptotic protein, according to instant invention.

In another aspect, the invention relates to a delivery particle comprising a nucleic acid for the controlled expression of a nucleic acid encoding a pro-apoptotic protein or a nucleic acid vector, as defined in the instant invention.

A still further aspect of the invention relates to a pharmaceutical composition comprising (i) a nucleic acid for the controlled expression of a nucleic acid encoding a pro-apoptotic protein, or a nucleic acid vector, or a delivery particle as defined herein, and (ii) a pharmaceutically acceptable vehicle.

In one aspect, the present invention relates to a host cell comprising the nucleic acid for the controlled expression of a nucleic acid encoding a pro-apoptotic protein or a nucleic acid vector, as defined herein.

In another aspect, the present invention relates to a nucleic acid for the controlled expression of a nucleic acid encoding a pro-apoptotic protein, as defined herein, for use as a medicament.

In one further aspect, the present invention relates to a nucleic acid for the controlled expression of a nucleic acid encoding a pro-apoptotic protein, as defined herein, for use as an active agent for inducing apoptosis into at least one target cell.

In a still further aspect, the present invention relates to a nucleic acid for the controlled expression of a nucleic acid encoding a pro-apoptotic protein, as defined herein, for use as an active agent for treating and/or preventing a tumor.

In another aspect, the present invention relates to a method for inducing apoptosis into at least one target cell comprising at least the step of administering to an individual in need thereof of the nucleic acid for the controlled expression of a nucleic acid encoding a pro-apoptotic protein or the nucleic acid vector, as defined herein.

In one aspect, the present invention relates to a method for treating and/or preventing a tumor comprising at least the step of administering to an individual in need thereof of the nucleic acid for the controlled expression of a nucleic acid encoding a pro-apoptotic protein or the nucleic acid vector, as defined herein.

Finally, another aspect of the invention relates to a kit for treating and/or preventing a tumor comprising:
- a pharmaceutical composition, as defined herein, and
- an anti-tumor compound.

LEGENDS OF THE FIGURES

FIG. 1: Scheme illustrating the GCN2-eIF2α-ATF4 signalling pathway. In response to EAA starvation, activated GCN2 phosphorylates eIF2α, leading to an up-regulation of the transcription factor ATF4 and its recruitment to AARE sequences to induce target gene expression.

Figure 2:

FIG. 2: Scheme illustrating the depiction of the AARE-gene construct: two copies of the AAREs (grey boxes) from Trb3 promoter and the Tk minimal promoter compose this construct.

Figure 3:
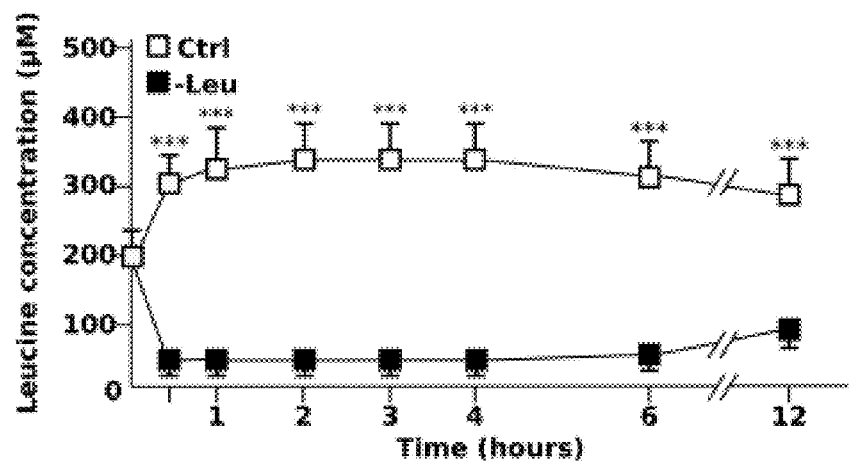

FIG. 3: Plot illustrating the plasma leucine concentration of mice. Following an overnight fasting in cleaned cages, mice were fed a control (Ctrl, open squares) or a diet devoid of leucine (−Leu, closed squares). Plasma was collected and leucine measured (Student's t-test: ***p<0.001 versus control diet, n=6 male mice; error bars: means+s.e.m.).

Figure 4:
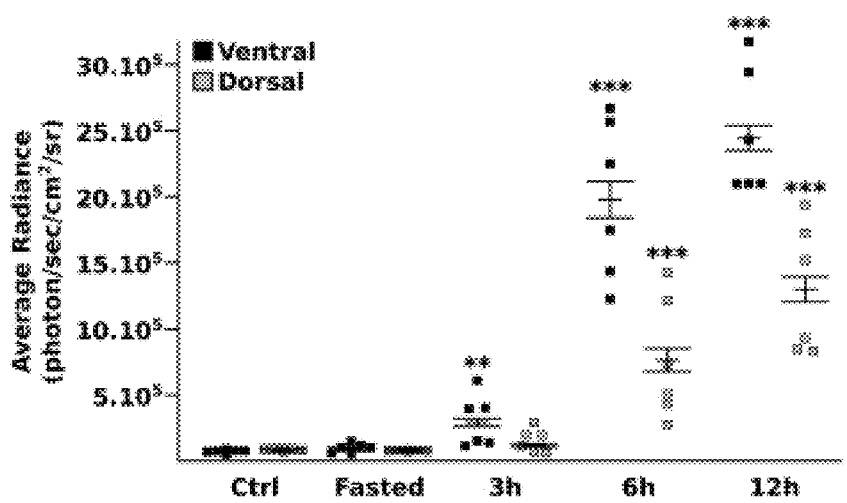

FIG. 4: Plot illustrating the measurement of luciferase expression in vivo. Transgenic mice were used in which the AARE-TK-luciferase construct was stably integrated. Following a 16 h-fasting period, transgenic mice were fed on a control diet (Ctrl) or on a diet devoid of leucine (−Leu). Bioluminescence imaging was performed for 3 to 12 hours after the beginning of the meal. Signal intensity as a result of photon detection is graded from red (highest number of photons) to blue (lowest intensity) (not shown). Light emission was then quantified using Regions Of Interest (ROI) covering the abdominal (ventral area, closed squares) or dorsal area (gray squares) (Student's t-test: *p<0.001, p<0.01 versus control diet, n=6 male mice; error bars: means+s.e.m.).

Figure 5:
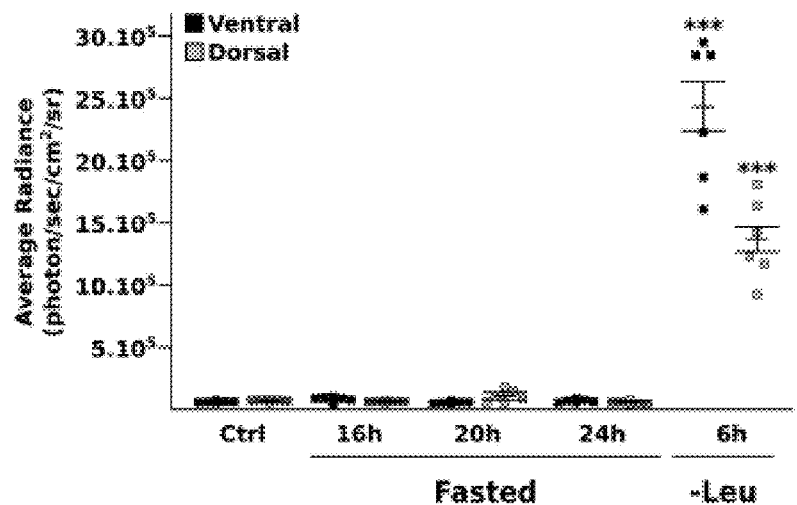

FIG. 5: Plot illustrating the measurement of luciferase expression in vivo following a long-fasting period. Following a 16 h, 20 h or 24 h-fasting period, transgenic mice were imaged for bioluminescence. Light emission was then quantified using Regions Of Interest (ROI) covering the abdominal (ventral area, closed squares) or dorsal area (gray squares) (Student's t-test: ***p<0.001 versus control diet, n=6 male mice; error bars: means+s.e.m.).

Figure 6:
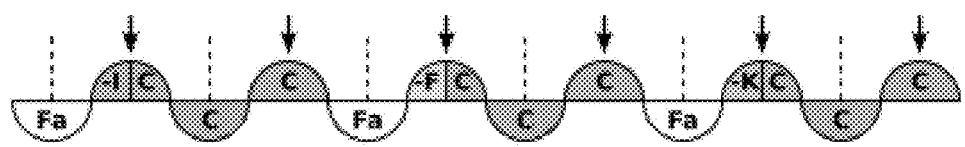

FIG. 6: Scheme illustrating the strategy for on/off expression regulation of a transgene via the AARE-Driven Expression system. Pulses of diets swapping the lacking amino acid (isoleucine, phenylalanine or lysine) were performed. AARE-Luc transgenic mice were subjected to three starvation sequences each including sequentially: a 12-hours fasting (white shape, Fa), a 6-hours feeding period on an EAA-deficient diet (gray shapes, −I; −F; −K) and a 30-hours of recovery period with a control diet (gray shape, C). A quarter circle represents 6 hours. Black arrows indicate time points for bioluminescence acquisition. Signal intensity as a result of photon detection is graded from red (highest number of photons) to blue (lowest intensity) (not shown).

Figure 7:
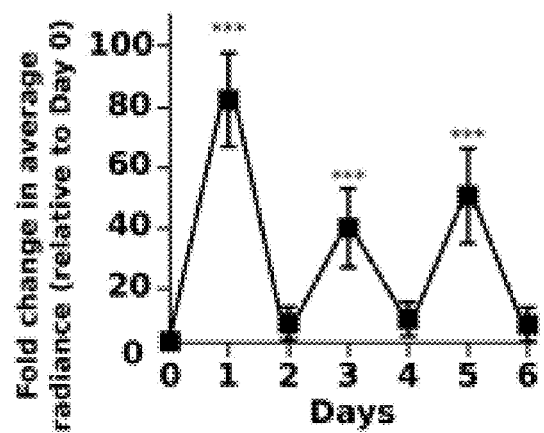

FIG. 7: Plot illustrating the light emission quantified using ROIs covering the abdominal area and bioluminescence fold induction along the time is represented in the conditions described in FIG. 6 (Student's t-test: ***p<0.001 versus day 0, n=6 male mice; error bars: means+s.e.m.).

Figure 8:
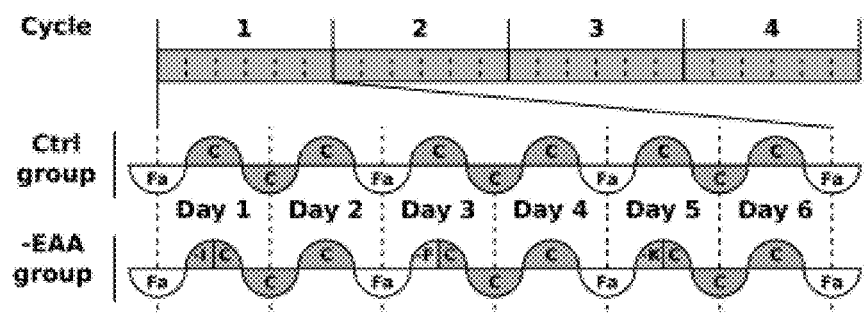

FIG. 8: Scheme illustrating the nutritional protocols for a 24-day utilization of the AARE-Driven Expression system.

Mice were subjected to a repetition of four times the nutritional cycle presented above (−EAA group). A control group (Ctrl group) was fed on a control diet only (see FIG. 6 for the references).

Figure 9:
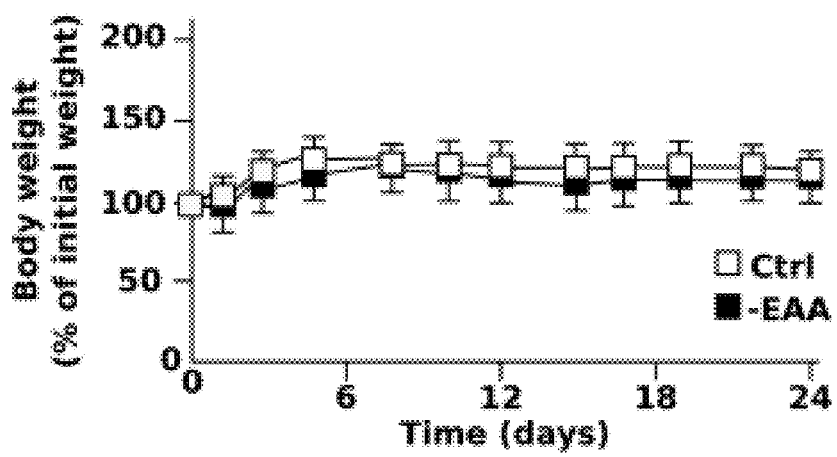

FIG. 9: Plot illustrating the body weight, expressed in percent of the initial value, observed during the nutritional protocols described in FIG. 8 above. Ctrl (open squares) and −EAA (closed squares) groups are depicted. No significant difference was observed between the 2 groups.

Figure 10:
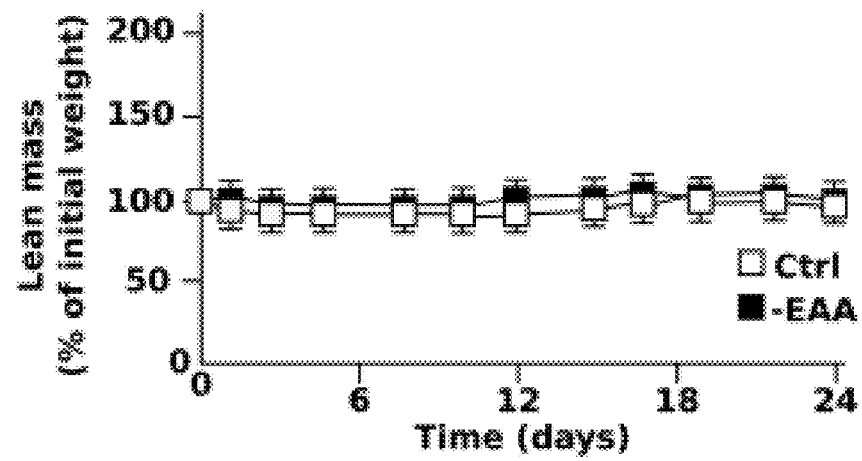

FIG. 10: Plot illustrating the lean mass, expressed in percent of the initial value, observed during the nutritional protocols described in FIG. 8 above. Ctrl (open squares) and −EAA (closed squares) groups are depicted. No significant difference was observed between the 2 groups.

Figure 11:
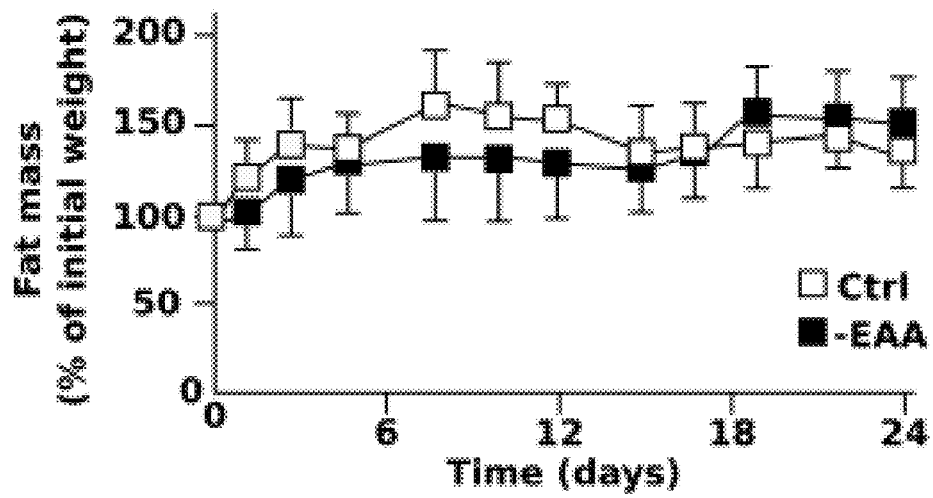

FIG. 11: Plot illustrating the fat mass, expressed in percent of the initial value, observed during the nutritional protocols described in FIG. 8 above. Ctrl (open squares) and −EAA (closed squares) groups are depicted. No significant difference was observed between the 2 groups.

Figure 12:
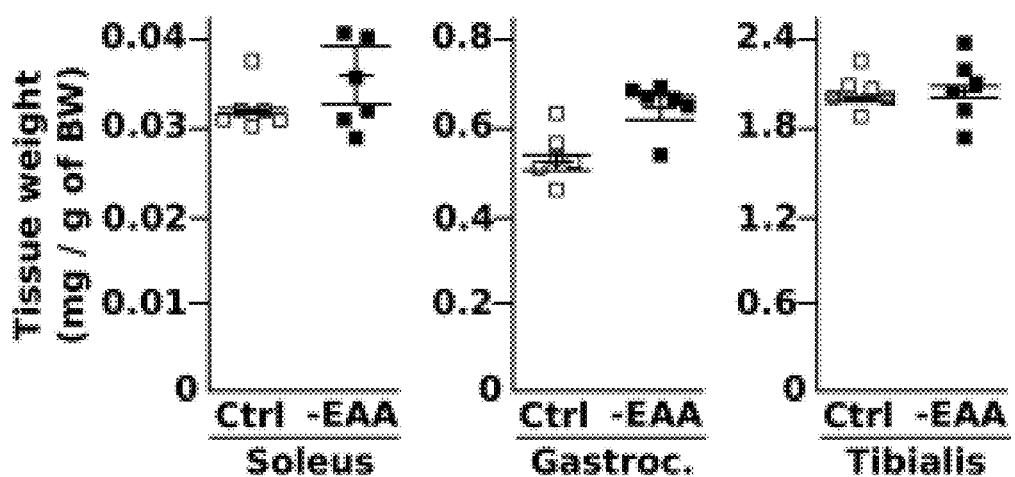

FIG. 12: Plot illustrating the muscles' tissue weight at the end of the nutritional protocols depicted in FIG. 8. Mice were sacrificed and three skeletal muscles (soleus, gastrocnemius and tibialis) were collected and weighted. Data are expressed in percent of control group. No significant difference was observed between the 2 groups.

Figure 13:
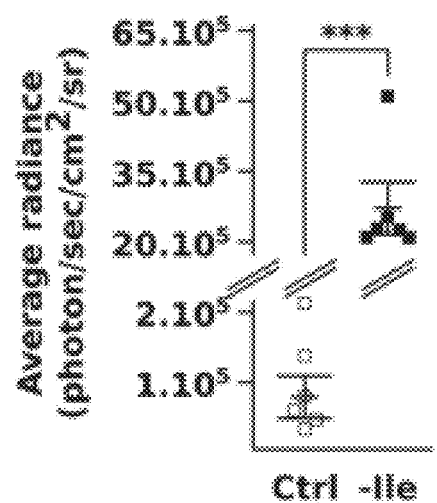

FIG. 13: Plot illustrating the average radiance measured from the bioluminescence imaging of mice following hydrodynamics-based DNA injection of the pGL3-AARE-Luc. Wild type mice received 25 micrograms of plasmid according the hydrodynamic injection method. Twenty-four hours later, mice were challenged with the nutritional protocol (−Ile diet following O/N starvation). Bioluminescence imaging was performed 6 hours after the beginning of the meal and light emission quantified using ROIs covering the abdominal area, the control group is represented by open squares and −Ile group is represented by closed squares (Student's t-test: ***$p<0.001$ versus Control diet, n=6 male mice; error bars: means+s.e.m.). Signal intensity as a result of photon detection is graded from red (highest number of photons) to blue (lowest intensity) (not shown).

Figure 14:
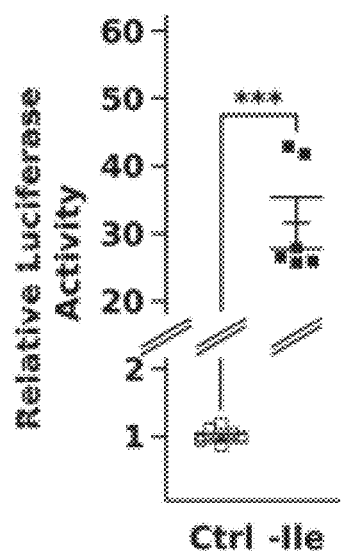

FIG. 14: Plot illustrating the relative luciferase activity measured from the livers of the mice treated as described in FIG. 13. Livers have been collected and imaged for bioluminescence and then the corresponding protein homogenates were assayed for luciferase activity determination. The control group is represented by open squares and −Ile group is represented by closed squares (Student's t-test: ***$p<0.001$ versus Control diet, n=6 male mice; error bars: means+s.e.m.).

Figure 15:
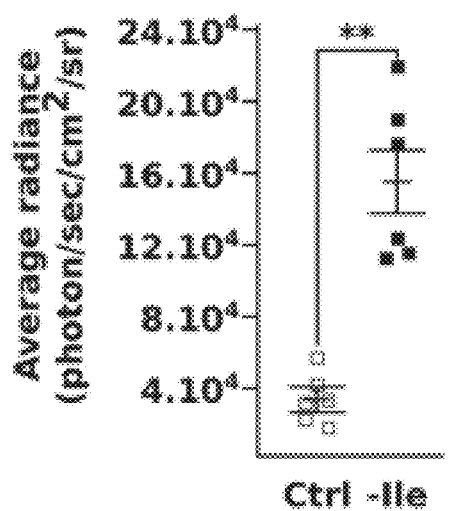

FIG. 15: Plot illustrating the intra-pancreatic delivery and induction of the AARE-Luc following lentiviral transduction. Administration of lentiviral particles containing the AARE-TK-Luc (LV-AARE-Luc) was performed into the pancreas of wild type mice. Ten days after injection, mice were challenged with the nutritional protocol (−Ile diet following O/N starvation). Light emission was quantified using ROIs covering the pancreatic area. Signal intensity as a result of photon detection is graded from red (highest number of photons) to blue (lowest intensity) (not shown). The control group is represented by open squares and −Ile group is represented by closed squares (Student's t-test: **$p<0.01$ versus Control diet, n=6 male mice; error bars: means+s.e.m.).

Figure 16:
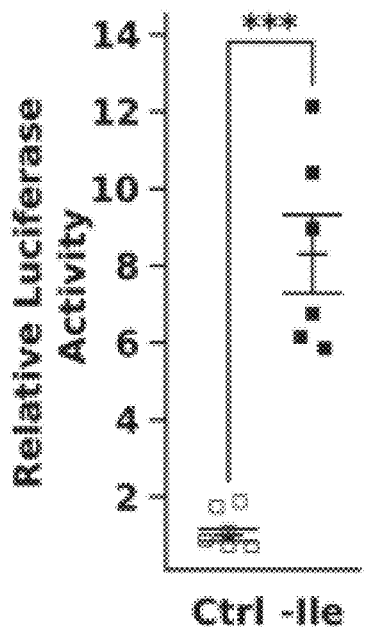

FIG. 16: Plot illustrating the relative luciferase activity measured from the pancreas of the mice treated as described in FIG. 15. The pancreas have been collected and imaged for bioluminescence and the corresponding protein homogenates were assayed for luciferase activity determination. The control group is represented by open squares and −Ile group is represented by closed squares (Student's t-test: ***$p<0.001$ versus Control diet, n=6 male mice; error bars: means+s.e.m.).

Figure 17:
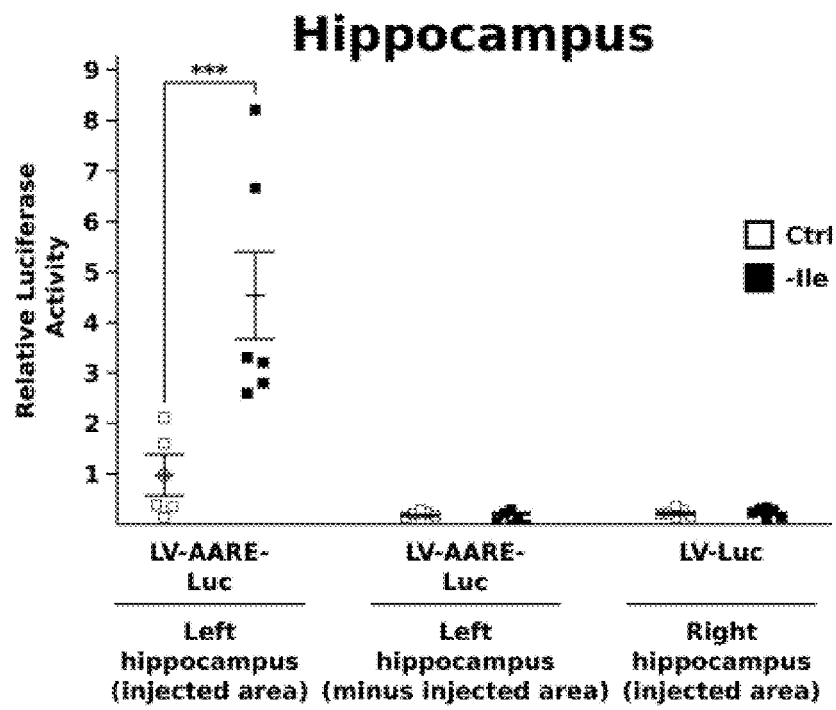

FIG. 17: Plot illustrating the intra-hippocampus delivery and induction of the AARE-Luc following lentiviral transduction. Stereotaxic administration of lentiviral particles containing AARE-Luc constructs was performed into the hippocampus of wild type mice. Two constructs were used: the AARE-TK-LUC construct (LV-AARE-Luc), injected in the left part of the hippocampus, and a control TK-LUC construct (LV-Luc) where AARE sequences were removed, infused in the right part. Ten days after injection, mice were challenged with the nutritional protocol (−Ile diet). Then, the two parts (left and right) of the hippocampus were collected, dissected and assayed for luciferase activity The control group is represented by open squares and −Ile group is represented by closed squares (Student's t-test: ***$p<0.001$ versus Control diet, n=6 male mice; error bars: means+s.e.m.).

Figure 18:
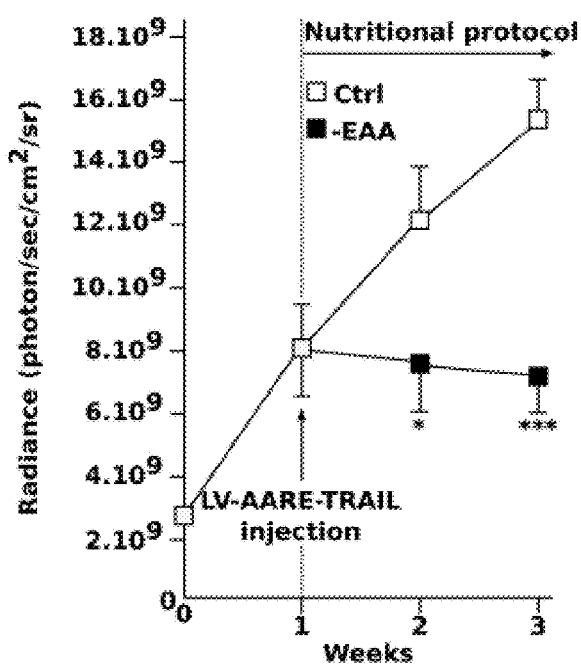

FIG. 18: Plot illustrating the tumor growth inhibition by TRAIL expression using the AARE-Driven Expression system. Gli36-luc cells ($2 \times 10^6$) were implanted subcutaneously in nude mice. A week after, intratumoral injections of the LV-AARE-TRAIL lentivirus were performed. Then, mice were subjected to the nutritional protocol described in FIG. 8: one group fed a control diet (Ctrl; open squares) and a second group fed with an alternation of EAA-deficient diets (−EAA; closed squares). Tumor growth was monitored by bioluminescence imaging on the first day after Gli36-luc implantation (T0) and subsequently every week. Signal intensity within the region of interest was quantified using ROIs covering the tumors (6 mice per group). Photon detection is graded from red (highest number of photons) to blue (lowest intensity) (not shown). Data were analysed using a two-way ANOVA with interaction, including nutritional protocol as one way and week as the second way *$p<0.05$; ***$p<0.001$, n=6 male mice; error bars: means+s.e.m.).

Figure 19:
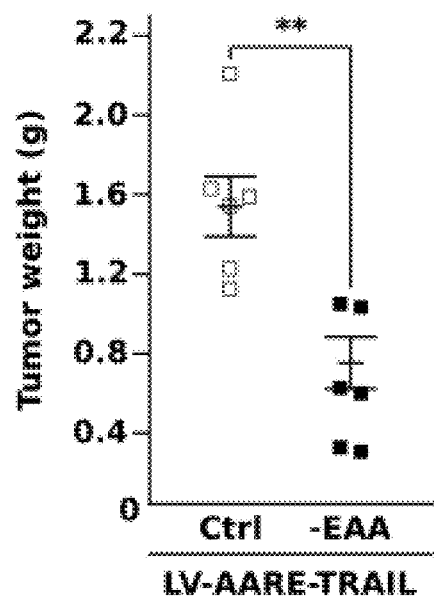

FIG. 19: Plot illustrating the tumors weight analysis from mice treated as in FIG. 18. At the end of the nutritional protocol, excised tumors were photographed and weighted. The control group is represented by open squares and −EAA group is represented by closed squares (Student's t-test: **$p<0.01$ versus Control diet, n=6 male mice; error bars: means+s.e.m.).

Figure 20:
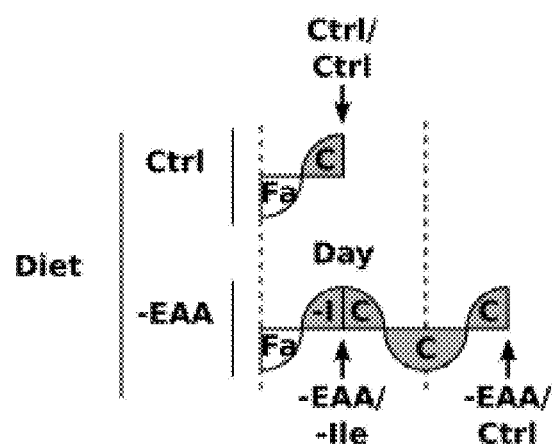

FIG. 20: Scheme illustrating the nutritional protocol for controlling the TRAIL-dependent apoptosis. At the end of the nutritional protocol, tumors from the Ctrl group fed a control diet (Ctrl/Ctrl) were excised at day 21. Within the −EAA group, half of the lot was sacrificed at day 21 whereas the other half was killed a day later. More specifically, three mice were first sacrificed after ingestion of a diet devoid of isoleucine (−EAA/−Ile) to detect induction of TRAIL expression. One day after, three other mice were killed to verify the extinction of TRAIL expression in response to a Ctrl diet. Black arrows indicate sacrifice time for each mentioned condition.

Figure 21:
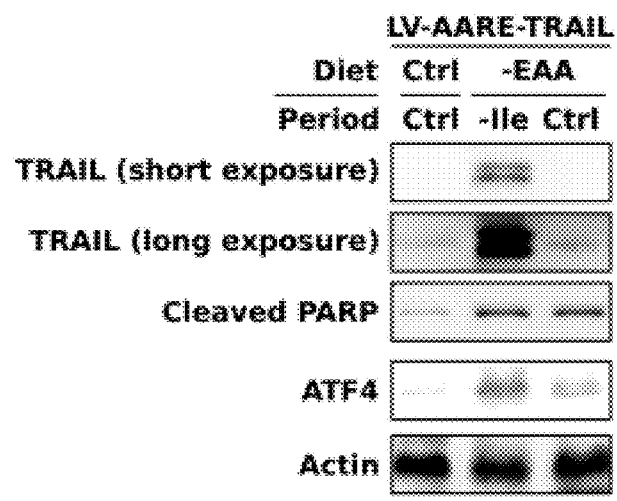

FIG. 21: Results of the analysis of the proteins homogenates from the excised tumors of mice treated as in FIG. 20. Proteins homogenates were analysed by western blot for detection of TRAIL (short and long exposures), cleaved-PARP, and ATF4 levels. Actin levels are shown as a loading control. Quantification of the western blot reveals that the level of TRAIL under EAA-diet was estimated to be over hundred fold more intense than the faint signal obtained under control conditions.

DETAILED DESCRIPTION OF THE INVENTION

Any citation mentioned herein is incorporated by reference.

The inventors assessed the remarkable features of the nutritional adaptation pathway to a diet deprived of one essential amino acid to achieve a regulatory system ideally suited for gene therapy. The inventors found that such a system, based on dietary specific amino acid starvation, does not require the expression of synthetic transcription factors or regulatory proteins nor the administration of pharmacological inducers. It is physiological, non-toxic and is amenable to clinical application. This novel nutrition-based regulatory system stands as a physiological approach with the ability to resolve one of the major remaining hurdles in human gene therapy and provides a "safety switch" for therapy approaches based on a "suicide strategy".

As shown in the examples herein, the flexibility of the AARE-Driven Expression System, in which each individual essential amino acid can act as a potential inducer. The inventors consider this point to be important in that it provides, even in the context of using a single cycle, a mean to select the "missing essential amino acid" according to the amplitude of the induction process that would be most appropriate for a particular experiment/situation.

A key part in the experimental data below concerns the pro-apoptotic protein TRAIL. The corresponding set of experiments were not only carried out to address issues dealing with cancer, but also as a model system to address the issues of background activities and the dynamics of the system. In other words, to be clinically relevant, a gene regulatory system should be regulated over a wide dose range of the inducer, within a safe dose of the vector, and exhibit a low level of background expression.

As it will arise from the description below, the AARE/suicide gene system is ideally suited to act as a suicide safety device, resulting in no possible immune response. Such a device is not necessary for the function of CAR T-cells, nor for the maturation/differentiation of stem/iPS cells. However, the presence of such a safety device would represent an indispensable safeguard in these corresponding therapies.

In addition, the AARE-based safety devices are perfectly secure by nature. An unforeseen expression of the suicide gene, which would destroy the CAR T-cells (or the iPSC-derived cells), would not arm the patient, in considering that he could easily receive another infusion of therapeutic "off-the-shelf" CAR T-cells.

Finally, the AARE-based suicide systems considerably broaden the field and development of safety switches. The whole family of caspases can be considered. Moreover, AARE suicide systems do not necessarily rely on protein of non-human origin to perform the suicide task. The expression of a suicide transgene must irremediably be followed by the execution of corresponding cell, in which the suicide gene is endogenously expressed, allowing no time for any immune reaction. Thus, the list of suicide genes could include "toxins" from various origins, provided that the gene products are not secreted and that their expressions are intimately associated with the killing of cells.

Nucleic Acid for the Controlled Expression of a Nucleic Acid Encoding a Pro-Apoptotic Protein A first aspect of the invention concerns a nucleic acid for the controlled expression of a nucleic acid encoding a pro-apoptotic protein in an individual, comprising:
a regulatory polynucleotide comprising a minimal promoter and at least one AARE (amino acid response element) nucleic acid, said regulatory polynucleotide being activated in an individual upon consumption of a diet deficient in at least one essential amino acid; and
a nucleic acid encoding a pro-apoptotic protein, which is placed under the control of the said regulatory polynucleotide.

Within the scope of the instant invention, the expression "pro-apoptotic protein" is intended to mean a protein that physiologically participates to programmed cellular death, or apoptosis, upon reception by the cell of a suitable signal.

Within the scope of the instant invention, the expression "controlled expression" expression is intended to mean that the expression is induced or turned "on" and shut down or turned "off" in a precise manner, with respect to the moment of induction, the duration of induction.

In certain embodiments, the expression of a nucleic acid encoding a pro-apoptotic protein may be measured by any suitable method available in the state of the art, including the measure of the mRNA expression, resulting from the transcription of the nucleic acid encoding a pro-apoptotic protein, and/or the measure of the pro-apoptotic protein expression.

In some embodiments, the measure of the pro-apoptotic protein expression may be performed by measuring the expression of the pro-apoptotic protein with anti-antibodies that specifically bind to said pro-apoptotic protein.

Within the scope of the present invention, an induced expression may be expressed as a time fold expression as compared to the basal, non-induced expression.

In some embodiments, the induced expression may vary from 2 fold to 10,000 fold, preferably from 4 fold to 500 fold, more preferably from 8 fold to 250 fold, most preferably from 10 fold to 100 fold, as compared to the basal expression.

Within the scope of the invention, from 2 fold to 10,000 fold includes 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 150 fold, 200 fold, 250 fold, 300 fold, 350 fold, 400 fold, 450 fold, 500 fold, 550 fold, 600 fold, 750 fold, 800 fold, 850 fold, 900 fold, 950 fold, 1,000 fold, 2,000 fold, 3,000 fold, 4,000 fold, 5,000 fold, 6,000 fold, 7,000 fold, 8,000 fold and 9,000 fold.

Within the scope of the invention, the expression "minimal promoter" is intended to mean a promoter including all the required elements to properly initiate transcription of a gene of interest positioned downstream. Within the scope of the invention, "minimal promoter" and "core promoter" are considered as equivalent expressions. A skilled artisan understands that the "minimal promoter" includes at least a transcription start site, a binding site for a RNA polymerase and a binding site for general transcription factors (TATA box).

Suitable minimal promoters are known for a skilled artisan.

In some embodiments, a minimal promoter suitable for carrying out the invention may be selected in a group comprising the promoter of the thymidine kinase, the promoter of the β-globin, the promoter for cytomegalovirus (CMV), the SV40 promoter and the like.

In some embodiments, the individual is a human or a non-human mammal, preferably a human.

In some embodiments, the non-human mammal is selected in a group comprising a pet such as a dog, a cat, a domesticated pig, a rabbit, a ferret, a hamster, a mouse, a rat and the like; a primate such as a chimp, a monkey, and the like; an economically important animal such as cattle, a pig, a rabbit, a horse, a sheep, a goat, a mouse, a rat.

Within the scope of the present invention, the expression "essential amino acid" includes histidine (His, H), isoleucine (Ile, I), leucine (Leu, L), Lysine (Lys, K), methionine (Met, M), phenylalanine (Phe, F), threonine (Thr, T), tryptophane (Trp, W) and valine (Val, V).

Within the scope of the invention, the expression "at least one essential amino acid" is intended to mean 1, 2, 3, 4, 5, 6, 7, 8 or 9 essential amino acid(s).

In some embodiments, a diet deficient in at least one essential amino acid may be administered to an individual for a time period of 5 min to 12 h, which includes 10 min, 15 min, 20 min, 25 min, 30 min, 45 min, 1 h, 1 h 30 min, 2 h, 2 h 30 min, 3 h, 3 h 30 min, 4 h, 4 h 30 min, 5 h, 5 h 30 min, 6 h, 6 h 30 min, 7 h, 7 h 30 min, 8 h, 8 h 30 min, 9 h, 9 h 30 min, 10 h, 10 h 30 min, 11 h, 11 h 30 min.

In some embodiments, a diet deficient in at least one essential amino acid may be administered to an individual once, twice, three times, four times, five times, six times a day, or more.

In some embodiments, a diet deficient in at least one essential amino acid may be administered to an individual every day, every other day, once a week, twice a week, three times per week.

In some embodiments, a diet deficient in at least one essential amino acid may be administered to an individual for a period of half a day, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days 20 days, or more.

In certain embodiments, the diet deficient in at least one essential amino acid may be administered to an individual once or twice a day.

In some embodiments, the diet deficient in at least one essential amino acid may be administered to an individual early in the morning, e.g. for breakfast, and then the individual may be administered a normal diet for lunch and dinner.

Within the scope of the instant invention, the expression "normal diet" is intended to mean a diet that is not deficient in any of the essential amino acids.

In some embodiments, a diet deficient in at least one essential amino acid may be repeated every week, every other week, every month, every month, or more.

In some embodiment, the diet deficient in at least one essential amino acid may be provided by an isoleucine-free, leucine-free and valine-free powdered food product commercially available from NUTRICA METABOLICS®, under the name MILUPA®. This diet is adapted to individual having Maple syrup urine disease, which disease appears to affect the branched chain amino acid metabolism.

In certain embodiment, a leucine-free, isoleucine-free or valine-free diet may be obtained by mixing the isoleucine-free, leucine-free and valine-free powder with an external source for the 2 remaining amino acids.

In certain embodiments, a phenylalanine-free diet may be provided a phenylalanine-free powder, commercially available from MEAD JOHNSON®. This diet is adapted to individual having phenylketonuria.

In practice, the powder is mixed with an adapted a liquid or a semi-solid food that is free of the desired essential amino acid.

In one embodiment, the amino acid response element (AARE) nucleic acid is selected in a group comprising a nucleic acid of sequence SEQ ID No: 1, SEQ ID No: 2, SEQ ID No: 3, SEQ ID No: 4 and SEQ ID No: 5.

Within the scope of the instant invention the expression "at least one AARE nucleic acid" includes at least 2, at least 3, at least 4 and at least 5 AARE nucleic acids. The expression "at least one AARE nucleic acid" thus includes 1, 2, 3, 4, 5, 6, 7, 8, 9, 10, 11, 12, 13, 14, 15, 16, 17, 18, 19, 20 AARE nucleic acids.

In certain embodiments, the regulatory polynucleotide comprises at least two AARE nucleic acids.

In some other embodiments, the regulatory polynucleotide comprises from one to twenty AARE nucleic acids, preferably from one to ten AARE nucleic acids.

In certain embodiments, the regulatory polynucleotide comprises from two to six AARE nucleic acids.

In some embodiments, the regulatory polynucleotide comprises two AARE nucleic acids selected in the group comprising a nucleic acid of sequence SEQ ID NO: 2 and SEQ ID NO: 4.

In some embodiments, the regulatory polynucleotide comprises six AARE nucleic acids of sequence SEQ ID NO: 1.

In certain embodiments, the at least two AARE nucleic acids may be identical or distinct.

In some embodiments, the regulatory polynucleotide comprised in the nucleic acid for the controlled expression of a nucleic acid encoding a pro-apoptotic protein may also be activated upon administration to an individual of halofuginone, tunicamycin, and the like, i.e. compounds which are known to have activating properties of the AARE nucleic acids.

Up to date, several families of pro-apoptotic proteins have been identified, among which may be cited the Bcl2 proteins family, the Bir-containing proteins family, the Card-containing proteins family, the caspase proteins family, the death domain-containing proteins family, the death effector domain-containing proteins family, the death ligand proteins family, the death receptor proteins family and the IAP antagonist proteins family.

With no limitation, the pro-apoptotic protein may be selected in a group comprising Apoptosis-inducing factor 1 (AIF, AIFM1), Adenylate kinase isoenzyme 2 (AK2), Annexin A1 (Annexin-1, Annexin I, Lipocortin I, Calpactin II, Chromobindin-9, p35, Phospholipase A2 inhibitory protein, ANXA1, ANX1, LPC1, ANNEXIN-1, LIPOCORTIN I), Apoptotic protease-activating factor 1 (APAF1, CED4), Nucleolar protein 3 (Myp, Nop30, ARC, NOL3), Cell death regulator Aven (AVEN, PDCD12), Bcl2 antagonist of cell death (Bcl-2-binding component 6, Bcl-XL/Bcl-2-associated death promoter, Bcl-2-like 8 protein, BAD, BCL2L8, BBC2), Bcl-2 homologous antagonist/killer (Apoptosis regulator BAK, Bcl-2-like 7 protein, BAK1, BAK2), Apoptosis regulator BAX (BAX, BCL2L4), Bcl-2-related protein A1 (BCL2A1,GRS, BFL1, BCL2L5, ACC-1, ACC-2), Apoptosis regulator Bcl-X (BCL2L1, BCLX, BCL2L, BCL-X, BCL-XL, BCL-XS), Apoptosis regulator Bcl-B (BCL2L10, DIVA, BOO, BCL-B), Bcl-2-like protein 11 (Bcl2-interacting mediator of cell death, BCL2L11, BOD, BIML, BIMEL, BIM), Bcl-2-related proline-rich protein (Bcl-2-like 12 protein, BCL2L12, BCL-2L12) Bcl-2-like 13 protein (Protein Mil1, Bcl-rambo, BCL2L13, MIL1 BCL-RAMBO, RAMBO), Apoptosis facilitator Bcl-2-like 14 protein (Apoptosis regulator Bcl-G, BCL2L14, BCLG, BCL-G), Apoptosis regulator Bcl-W (Bcl-2-like 2 protein, BCL2L2, KIAA0271, BCL-W), BH3-interacting domain death agonist (p22 BID, BID), Bcl-2-interacting killer (Apoptosis inducer NBK, BP4, BIP1, BIK, NBK/BLK), Baculoviral IAP repeat-containing protein 1 (Neuronal apoptosis inhibitory protein, BIRC1, NLRB1), Baculoviral IAP repeat-containing protein 3 (Inhibitor of apoptosis protein 1, HIAP-1, HIAP1, C-IAP2, TNFR2-TRAF-signaling complex protein 1, IAP homolog C, Apoptosis inhibitor 2, API2, RING finger protein 49, BIRC3, CIAP2, HIAP-1, MIHC, RNF49, MALT2), Baculoviral IAP repeat-containing protein 5 (Apoptosis inhibitor surviving, Apoptosis inhibitor 4, BIRC5), Bcl-2-modifying factor (BMF, FLJ00065), BCL2/adenovirus E1B 19 kDa protein-interacting protein 3 (BNIP3, NIP3), $BCL^2$/adenovirus E1B 19 kDa protein-interacting protein 3-like (NIP3-like protein X, NIP3L, BCL2/adenovirus E1B 19 kDa protein-interacting protein 3A, Adenovirus E1B19K-binding protein B5, BNIP3L, NIX, BNIP3A), Bcl-2-related ovarian killer protein (Hbok, BOK, BCL2L9, BOKL, MGC4631), Calreticulin Precursor (CRP55, Calregulin, HACBP, ERp60, grp60, CALR), Caspase-1 Precursor (CASP-1, EC 3.4.22.36, Interleukin-1 beta convertase, IL-1BC, Interleukin-1 beta-converting enzyme, IL-1 beta-converting enzyme, ICE, p45, CASP1, ICE, CASPASE-1, CASPASE 1, CASP1), Caspase-10 Precursor (CASP-10, EC 3.4.22.63, ICE-like apoptotic protease 4, Apoptotic protease Mch-4, FAS-associated death domain protein interleukin-1B-converting enzyme 2, FLICE2, CASP10, MCH4), Inactive caspase-12 (CASP-12), Caspase-2 Precursor (CASP-2, EC 3.4.22.55, ICH-1 protease, Neural precursor cell expressed developmentally down-regulated protein 2, NEDD-2, CASP2, ICH1), Caspase-3 Precursor (CASP-3, EC 3.4.22.56, Apopain, Cysteine protease CPP32, CPP-32, Yama protein, SREBP cleavage activity 1, SCA-1, CASP3, CPP32, CPP32B, YAMA, APOPAIN), Caspase-4 Precursor (CASP-4, EC 3.4.22.57, ICH-2 protease, TX protease, ICE(rel)-II, CASP4, ICE (REL)II, ICH-2, TX), Caspase-5 Precursor (CASP-5, EC 3.4.22.58, ICH-3 protease,TY protease, ICE(rel)-III, CASP5, ICE(REL)III), Caspase-6 Precursor (CASP-6, EC 3.4.22.59, Apoptotic protease Mch-2, CASP6, MCH2), Caspase-7 Precursor (CASP-7, EC 3.4.22.60, ICE-like apoptotic protease 3, ICE-LAP3, Apoptotic protease Mch-3, CMH-1, CASP7, MCH3), Caspase-8 Precursor (CASP-8, EC 3.4.22.61, ICE-like apoptotic protease 5, MORT1-associated CED-3 homolog, MACH, FADD-homologous ICE/CED-3-like protease, FADD-like ICE, FLICE, Apoptotic cysteine protease, Apoptotic protease Mch-5, CAP4, CASP8, MCH5), Caspase-9 Precursor (CASP-9, EC 3.4.22.62, ICE-like apoptotic protease 6, ICE-LAP6, Apoptotic protease Mch-6, Apoptotic protease-activating factor 3, APAF-3, CASP9, CASPASE-9, CASPASE 9, CASP9, MCH6, ICE-LAP6, APAF-3), Caspase-14 Precursor (CASP-14, EC 3.4.22, CASPASE-14, CASP14, CASPASE 14, MICE, MGC119078, MGC119079), CASP8 and FADD-like apoptosis regulator Precursor (Cellular FLICE-like inhibitory protein, c-FLIP, Caspase-eight-related protein, Casper, Caspase-like apoptosis regulatory protein, CLARP, MACH-related inducer of toxicity, MRIT, Caspase homolog, CASH, Inhibitor of FLICE, I-FLICE, FADD-like antiapoptotic molecule 1, FLAME-1, Usurpin, CFLAR, CASPER, CLARP, FLAME, FLIP, MRIT), Baculoviral IAP repeat-containing protein 2 (Inhibitor of apoptosis protein 2, HIAP-2, C-IAP1, TNFR2-TRAF-signaling complex protein 2, IAP homolog B, RING finger protein 48, CIAP1, BIRC2, CIAP1, HIAP-2, MIHB, RNF48), Death domain-containing protein CRADD (Caspase and RIP adapter with death domain, RIP-associated protein with a death domain, CRADD, RAIDD), Exportin-2 (Exp2, Importin-alpha re-exporter, Chromosome segregation 1-like protein, Cellular apoptosis susceptibility protein, CSE1L, CAS, XPO2, CSE1), Probable ubiquitin carboxyl-terminal hydrolase CYLD (EC 3.1.2.15, Ubiquitin thioesterase CYLD, Ubiquitin-specific-processing protease CYLD, Deubiquitinating enzyme CYLD, CYLD), Cytochrome c (CYTOCHROME C, HCS, CYCS), Diablo homolog, mitochondrial Precursor (Second mitochondria-derived activator of caspase, Smac protein, Direct IAP-binding protein with low pI, DIABLO, SMAC, DIABLO-S, FLJ25049, FLJ10537), Endonuclease G, mitochondrial Precursor (Endo G, EC 3.1.30.-), Protein FADD (FAS-associated death domain protein, FAS-associating death domain-containing protein, Mediator of receptor induced toxicity, FADD, MORT1, GIG3), Tumor necrosis factor receptor superfamily member 6 Precursor (FASLG receptor, Apoptosis-mediating surface antigen FAS, Apo-1 antigen, CD95 antigen, FAS, CD95, APO-1), Tumor necrosis factor ligand superfamily member 6 (Fas antigen ligand, Fas ligand, CD95L protein, Apoptosis antigen ligand, APTL, CD178 antigen, FASL, CD178, FAS LIGAND), Glyceraldehyde-3-phosphate dehydrogenase (GAPDH), Granzyme B Precursor (EC 3.4.21.79, Granzyme-2, T-cell serine protease 1-3E, Cytotoxic T-lymphocyte proteinase 2, Lymphocyte protease, SECT, Cathepsin G-like 1, CTSGL1, CTLA-1, Fragmentin-2, Human lymphocyte protein, HLP, C11, GZMB, GRB, GRANZYME B), Activator of apoptosis harakiri (Neuronal death protein DP5, BH3-interacting domain-containing protein 3, HRK, DP5), Serine protease HTRA2, mitochondrial Precursor (EC 3.4.21.108, High temperature requirement protein A2, HtrA2, Omi stress-regulated endoprotease, Serine proteinase OMI, Serine protease 25, HTRA2, OMI, PARK13), Intercellular adhesion molecule 3 Precursor (ICAM-3, ICAM-R, CDw50, CD50 antigen), Leucine-rich repeat and death domain-containing protein (p53-induced protein with a death domain, LRDD, PIDD, MGC16925, DKFZP434D229), Prolow-density lipoprotein receptor-related protein 1 Precursor (LRP, Alpha-2-macroglobulin receptor, A2MR, Apolipoprotein E receptor, APOER, CD91 antigen, LRP1, CD91), Mucosa-associated lymphoid tissue lymphoma translocation protein 1 (EC 3.4.22.-, MALT lymphoma-associated translocation, Paracaspase, MALT1), Mitogen-activated protein kinase 8 (EC 2.7.11.24, Stress-activated protein kinase JNK1, c-Jun N-terminal kinase 1, JNK-46, MAPK8, JNK, JNK1, SAPK1,) Induced myeloid leukemia cell differentiation protein Mcl-1 (Bcl-2-related protein EAT/mcl1, mcl1/EAT, MCL1, BCL2L3), Modulator of apoptosis 1 (MAP-1, MAP1, Paraneoplastic antigen Ma4, MOAP1, PNMA4), LRR and PYD domains-containing protein 1 (Death effector filament-forming ced-4-like apoptosis protein, Nucleotide-binding domain and caspase recruitment domain, Caspase recruitment domain-containing protein 7, NLRP1, KIAA0926, DKFZP58601822, CARD7, NAC, CLR17.1, DEFCAP, NACHT), LRR and PYD domains-containing protein 3 (Cold autoinflammatory syndrome 1 protein, Cryopyrin, PYRIN-containing APAF1-like protein 1, Angiotensin/vasopressin receptor AII/AVP-like, NLRP3, AGTAVPRL, AII, AVP, FCAS, FCU, NALP3, PYPAF1, MWS, CLR1.1, NACHT), Phorbol-12-myristate-13-acetate-induced protein 1 (PMA-induced protein 1, Immediate-early-response protein APR, NOXA, PMAIP1, APR), Dynamin-like 120 kDa protein, mitochondrial Precursor (Optic atrophy protein 1, OPA1), Acidic leucine-rich nuclear phosphoprotein 32 family member A (Potent heat-stable protein phosphatase 2A inhibitor I1PP2A, Acidic nuclear phosphoprotein pp32, Leucine-rich acidic nuclear protein, Lanp, Putative HLA-DR-associated protein I, PHAPI, Mapmodulin, PHAP, ANP32A, LANP, PP32, I1PP2A, MAPM, MAPMODULIN), Bcl-2-binding component 3 (p53 up-regulated modulator of apoptosis, JFY-1, PUMA, BBC3), Apoptosis-associated speck-like protein containing a CARD (hASC, PYD and CARD domain-containing protein, Target of methylation-induced silencing 1, Caspase recruitment domain-containing protein 5, PYCARD, TMS-1, CARD5, ASC), Receptor-interacting serine/threonine-protein kinase 1 (EC 2.7.11.1, Serine/threonine-protein kinase RIP, Cell death protein RIP, Receptor-interacting protein, RIPK1, RIP), Receptor-interacting serine/threonine-protein kinase 3 (EC 2.7.11.1, RIP-like protein kinase 3, Receptor-interacting protein 3, RIP-3, RIPK3), Endophilin-B 1 (SH3 domain-containing GRB2-like protein B 1, Bax-interacting factor 1, Bif-1, SH3GLB1, CGI-61, KIAA0491, BIF-1), Tumor necrosis factor Precursor (TNF-alpha, Tumor necrosis factor ligand superfamily member 2, TNF-α, Cachectin, TNF, TNFSF2, DIF, TNF-ALPHA), Tumor necrosis factor receptor superfamily member 1A Precursor (p60, TNF-R1, TNF-RI, TNFR-I, p55, CD120a antigen, TNFRSF1A, TNF-R, TNFAR, TNFR60, TNF-R-I, CD120A, TNF-R55), Tumor necrosis factor receptor superfamily member 1B Precursor (Tumor necrosis factor receptor 2, TNF-R2, Tumor necrosis factor receptor type II, p'75, p80 TNF-alpha receptor, CD120b antigen, Etanercept, TNFRSF1B, TNFBR, TNFR80, TNF-R75, TNF-R-II, P75, CD120B), Tumor necrosis factor ligand superfamily member 10 (TNF-related apoptosis-inducing ligand, Protein TRAIL, Apoptosis ligand 2, Apo-2 ligand, Apo-2L, Apo2L, CD253 antigen, TNFSF10, TRAIL, APO-2L, APO2L TL2, CD253), Cellular tumor antigen p53 (Tumor suppressor p53, Phosphoprotein p53, Antigen NY-CO-13, TP53, P53, LFS1), Tumor necrosis factor receptor type 1-associated DEATH domain protein (TNFR1-associated DEATH domain protein, TNFRSF1A-associated via death domain, TRADD, HS.89862), TNF receptor-associated factor 1 (Epstein-Barr virus-induced protein 6, TRAF1, EBI6), TNF receptor-associated factor 2 (Tumor necrosis factor type 2 receptor-associated protein 3, TRAF2, TRAP3), Tumor necrosis factor receptor superfamily member 10A Precursor (Death receptor 4, TNF-related apoptosis-inducing ligand receptor 1, TRAIL receptor 1, TRAIL-R1, CD261 antigen, TRAIL-R1, DR4, TNFRSF10A, DR4, CD261), Tumor necrosis factor receptor superfamily member 10B Precursor (Death receptor 5, TNF-related apoptosis-inducing ligand receptor 2, TRAIL receptor 2, TRAIL-R2, CD262 antigen TRAIL-R2, TNFRSF10B, TNFRSF10B, TRAIL-R2, DR5, KILLER, TRICK2A, TRICK2B, APO-2, CD262), Tumor necrosis factor receptor superfamily member 10C Precursor (Decoy receptor 1, DcR1, Decoy TRAIL receptor without death domain, TNF-related apoptosis-inducing ligand receptor 3, TRAIL receptor 3, TRAIL-R3, Trail receptor without an intracellular domain, Lymphocyte inhibitor of TRAIL, Antagonist decoy receptor for TRAIL/Apo-2L, CD263 antigen, TRAIL-R3/TNFSF10C, TNFRSF10C, TRAIL-R3, DCR1, LIT, TRID, CD263), TNF-related apoptosis-inducing ligand receptor 4 (TRAIL receptor 4, TRAIL-R4, Tumor necrosis factor receptor superfamily member 10D Precursor, Decoy receptor 2, DcR2, TRAIL receptor with a truncated death domain, CD264 antigen, TRAIL-R4, TNFRSF10D, TNFRSF10D, DCR2, TRUNDD, CD264), XIAP-associated factor 1 (BIRC4-binding protein, XAF1) and Baculoviral IAP repeat-containing protein 4 (EC 6.3.2.-, E3 ubiquitin-protein ligase XIAP, Inhibitor of apoptosis protein 3, X-linked inhibitor of apoptosis protein, X-linked IAP, IAP-like protein, XIAP, HILP).

In some embodiments, the pro-apoptotic protein is selected in a group comprising TRAIL, FAS receptor, FAS-associated protein, FADD, caspase 1, caspase 3, caspase 7, caspase 8 and caspase 9.

In certain embodiments, the pro-apoptotic protein is TRAIL.

Nucleic Acid Vector

In another aspect, the invention also concerns a nucleic acid vector for the controlled expression of a nucleic acid encoding a pro-apoptotic protein, comprising a nucleic acid for the controlled expression of a nucleic acid encoding a pro-apoptotic protein, as defined herein.

In some embodiments, the nucleic acid for the controlled expression of a nucleic acid encoding a pro-apoptotic protein according to the invention is incorporated in a vector that is suitable for gene therapy.

Within the scope of the instant invention, the expression "vector that is suitable for gene therapy" is intended to mean that the vector comprises the essential elements for achieving the expression of the nucleic acid encoding a pro-apoptotic protein in a target cell.

In certain embodiments, the vector is a viral vector.

In some embodiments, a viral vector is selected in a group comprising an adenovirus, an adeno-associated virus, an alphavirus, a herpesvirus, a lentivirus, a non-integrative lentivirus, a retrovirus and a vaccinia virus.

Delivery Particle

In a still other aspect, the invention further concerns a delivery particle comprising a nucleic acid for the controlled expression of a nucleic acid encoding a pro-apoptotic protein or a nucleic acid vector, as defined herein.

In certain embodiments, the delivery particle may be in the form of a lipoplex, comprising cationic lipids; a lipid nano-emulsion; a solid lipid nanoparticle; a peptide based particle; a polymer based particle, in particular comprising natural and/or synthetic polymers.

In some embodiments, a polymer based particle may comprise a protein; a peptide; a polysaccharide, in particular chitosan.

In some embodiments, a polymer based particle may comprise a synthetic polymer, in particular, a polyethylene imine (PEI), a dendrimer, a poly (DL-Lactide) (PLA), a poly(DL-Lactide-co-glycoside) (PLGA), a polymethacrylate and a polyphosphoesters.

In some embodiments, the delivery particle further comprises at its surface one or more ligands suitable for binding to a target receptor exposed at the membrane of a targeted cell.

Pharmaceutical Composition

Another aspect of the present invention concerns a pharmaceutical composition comprising (i) a nucleic acid for the controlled expression of a nucleic acid encoding a pro-apoptotic protein, or a nucleic acid vector or a delivery particle, as defined herein, and (ii) a pharmaceutically acceptable vehicle.

The formulation of pharmaceutical compositions according to the instant invention is well known to persons skilled in the art.

As referred herein, a nucleic acid for the controlled expression of a nucleic acid encoding a pro-apoptotic protein, or a nucleic acid vector or a delivery particle, as defined in the present disclosure, may represent the active agent.

In some embodiments, the pharmaceutical composition may comprise a nucleic acid for the controlled expression of a nucleic acid encoding a pro-apoptotic protein, or a nucleic acid vector or a delivery particle, as defined in the present disclosure, as the only active agent.

In some embodiments, a suitable pharmaceutically acceptable vehicle according to the invention includes any and all conventional solvents, dispersion media, fillers, solid carriers, aqueous solutions, coatings, antibacterial and antifungal agents, isotonic and absorption delaying agents, and the like.

In certain embodiments, suitable pharmaceutically acceptable vehicles may include, water, saline, phosphate buffered saline, dextrose, glycerol, ethanol and a mixture thereof.

In some embodiments, pharmaceutically acceptable vehicles may further comprise minor amounts of auxiliary substances such as wetting or emulsifying agents, preservatives or buffers, which enhance the shelf life or effectiveness of the cells. The preparation and use of pharmaceutically acceptable vehicles is well known in the art.

Except insofar as any conventional media or agent is incompatible with the active ingredient, use thereof in the pharmaceutical compositions of the present invention is contemplated.

In some embodiments, the pharmaceutical composition may be administered to an individual in need thereof by any route, i.e. by an oral administration, a topical administration or a parenteral administration, e.g., by injection, including a sub-cutaneous administration, a venous administration, an arterial administration, in intra-muscular administration, an intra-ocular administration and an intra-auricular administration.

In certain embodiments, the administration of the pharmaceutical composition by injection may be directly performed in the target tissue of interest, in particular in order to avoid spreading of the nucleic acid or the nucleic acid vector comprised in the said pharmaceutical composition.

The inventors consider that this is particularly important when the brain tissue is target. Nucleic acid vector infusions can be conducted with great precision in specific parts of the brain tissue, e.g. by the mean of taking advantage of a magnetic resonance scanner, in particular using frameless stereotactic aiming devices. The use of MRI-guidance and new stereotactic aiming devices, have now established a strong foundation for neurological gene therapy to become an accepted procedure in interventional neurology.

Other modes of administration employ pulmonary formulations, suppositories, and transdermal applications.

In some embodiments, an oral formulation according to the invention includes usual excipients, such as, for example, pharmaceutical grades of mannitol, lactose, starch, magnesium stearate, sodium saccharine, cellulose, magnesium carbonate, and the like.

In some embodiments, an effective amount of said compound is administered to said individual in need thereof.

Within the scope of the instant invention, an "effective amount" refers to the amount of said compound that alone stimulates the desired outcome, i.e. alleviates or eradicates the symptoms of the encompassed disease, in particular a cancer.

It is within the common knowledge of a skilled artisan to determine the effective amount of a nucleic acid for the controlled expression of a nucleic acid encoding a pro-apoptotic protein, or a nucleic acid vector or a delivery particle in order to observe the desired outcome.

Within the scope of the instant invention, the effective amount of the compound to be administered may be determined by a physician or an authorized person skilled in the art and can be suitably adapted within the time course of the treatment.

In certain embodiments, the effective amount to be administered may depend upon a variety of parameters, including the material selected for administration, whether the administration is in single or multiple doses, and the individual's parameters including age, physical conditions, size, weight, gender, and the severity of the disease to be treated.

In certain embodiments, an effective amount of the active agent may comprise from about 0.001 mg to about 3000 mg, per dosage unit, preferably from about 0.05 mg to about 100 mg, per dosage unit.

Within the scope of the instant invention, from about 0.001 mg to about 3000 mg includes, from about 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg and 2950 mg, per dosage unit.

In certain embodiments, the active agent may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day.

In some particular embodiments, an effective amount of the active agent may comprise from about $1 \times 10^5$ to about $1 \times 10^{15}$ copies of the nucleic acid for the controlled expression of a nucleic acid encoding a pro-apoptotic protein, or the nucleic acid vector or the delivery particle, as defined in the present disclosure, per dosage unit.

Within the scope of the instant invention, from about $1 \times 10^5$ to about $1 \times 10^{15}$ copies includes $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$ $8 \times 10^7$ $9 \times 10^7$ $1 \times 10^8$ $2 \times 10^8$ $3 \times 10^8$ $4 \times 10^8$ $5 \times 10^8$ $6 \times 10^8$ $7 \times 10^8$ $8 \times 10^8$ $9 \times 10^8$ $1 \times 10^9$ $2 \times 10^9$ $3 \times 10^9$ $4 \times 10^9$ $5 \times 10^9$ $6 \times 10^9$ $7 \times 10^9$ $8 \times 10^9$ $9 \times 10^9$ $1 \times 10^{10}$ $2 \times 10^{10}$ $3 \times 10^{10}$, $4 \times 10$ $5 \times 10^{10}$ $6 \times 10^{10}$ $7 \times 10^{10}$ $8 \times 10^{10}$, $9 \times 10^{10}$, $1 \times 10^{11}$ $2 \times 10^{11}$ $3 \times 10^{11}$ $4 \times 10^{11}$ $5 \times 10^{11}$ $6 \times 10^{11}$ $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$ copies, per dosage unit.

Host Cell

In a further aspect, the invention concerns a host cell comprising the nucleic acid for the controlled expression of a nucleic acid encoding a pro-apoptotic protein or a nucleic acid vector, as defined herein.

In some embodiments, the host cell is a eukaryotic cell.

Within the scope of the invention, a "eukaryotic cell" encompasses an animal cell, preferably a mammal cell and more preferably a human cell.

In some preferred embodiments, the eukaryotic cell is a mammal cell, preferably a human cell.

In certain embodiments, a host cell according to the instant invention may encompass, without limitation, a cell of the central nervous system, an epithelial cell, a muscular cell, an embryonic cell, a germ cell, a stem cell, a progenitor cell, a hematopoietic stem cell, a hematopoietic progenitor cell, an induced Pluripotent Stem Cell (iPSC).

In some particular embodiments, the host cell is not a stem cell, a progenitor cell, a germinal cell or an embryonic cell.

In some embodiments, the host cell may belong to a tissue selected in a group comprising a muscle tissue, a nervous tissue, a connective tissue, and an epithelial tissue.

In some embodiments, the host cell may belong to an organ selected in a group comprising a bladder, a bone, a brain, a breast, a central nervous system, a cervix, a colon, an endometrium, a kidney, a larynx, a liver, a lung, an oesophagus, an ovarian, a pancreas, a pleura, a prostate, a rectum, a retina, a salivary gland, a skin, a small intestine, a soft tissue, a stomach, a testis, a thyroid, an uterus, a vagina.

In certain embodiments, a host cell according to the instant invention may be a cancer cell, in particular a cancer cell selected in a group comprising a leukaemia cell, a carcinoma cell, a sarcoma cell, a lymphoma cell, a craniopharyngioma cell, a bastoma cell, a melanoma cell, a glioma cell and a mesothelioma cell.

In some embodiments, the cancer cell is selected in a group comprising an esthesioneuro-blastoma cell, a glioblastoma cell, a hepatoblastoma cell, a medulloblastoma cell, a nephroblastoma cell, a neuroblastoma cell, a pancreatoblastoma cell, a pleuropulmonary blastoma cell, a retinoblastoma cell.

Uses

Another aspect of the invention concerns a nucleic acid for the controlled expression of a nucleic acid encoding a pro-apoptotic protein, as defined herein, for use as a medicament.

In one aspect, the invention also relates to the use of a nucleic acid for the controlled expression of a nucleic acid encoding a pro-apoptotic protein, as defined herein, for the preparation or the manufacture of a medicament.

In a still other aspect, the invention concerns a nucleic acid for the controlled expression of a nucleic acid encoding a pro-apoptotic protein, as defined herein, for use as an active agent for inducing apoptosis into at least one target cell.

Another aspect of the invention further relates to the use of a nucleic acid for the controlled expression of a nucleic acid encoding a pro-apoptotic protein, as defined herein, as an active agent for inducing apoptosis into at least one target cell.

In certain embodiments, the induction of apoptosis may be performed in vivo, in vitro or ex vivo.

In one embodiment, the target cell is a tumor cell.

In some embodiments, the tumor cell is selected in a group comprising a cell from a bladder cancer, a bone cancer, a brain cancer, a breast cancer, a cancer of the central nervous system, a cancer of the cervix, a cancer of the upper aero digestive tract, a colorectal cancer, an endometrial cancer, a germ cell cancer, a glioblastoma, a Hodgkin lymphoma, a kidney cancer, a laryngeal cancer, a leukaemia, a liver cancer, a lung cancer, a myeloma, a nephroblastoma (Wilms tumor), a neuroblastoma, a non-Hodgkin lymphoma, an oesophageal cancer, an osteosarcoma, an ovarian cancer, a pancreatic cancer, a pleural cancer, a prostate cancer, a retinoblastoma, a skin cancer (including a melanoma), a small intestine cancer, a soft tissue sarcoma, a stomach cancer, a testicular cancer and a thyroid cancer.

In one aspect, the present invention concerns a nucleic acid for the controlled expression of a nucleic acid encoding a pro-apoptotic protein, as defined herein, for use as an active agent for treating and/or preventing a tumor.

In some embodiments, the tumor is selected in a group comprising a bladder cancer, a bone cancer, a brain cancer, a breast cancer, a cancer of the central nervous system, a cancer of the cervix, a cancer of the upper aero digestive tract, a colorectal cancer, an endometrial cancer, a germ cell cancer, a glioblastoma, a Hodgkin lymphoma, a kidney cancer, a laryngeal cancer, a leukaemia, a liver cancer, a lung cancer, a myeloma, a nephroblastoma (Wilms tumor), a neuroblastoma, a non-Hodgkin lymphoma, an oesophageal cancer, an osteosarcoma, an ovarian cancer, a pancreatic cancer, a pleural cancer, a prostate cancer, a retinoblastoma, a skin cancer (including a melanoma), a small intestine cancer, a soft tissue sarcoma, a stomach cancer, a testicular cancer and a thyroid cancer.

In some embodiments, a skilled in the art may understand that ex vivo manipulations and/or therapy may be encompassed within the scope of the instant invention, which would include stem cells and progenitor cells, hematopoietic stem and progenitor cells, induced Pluripotent Stem Cell (iPSC), and adult cells from different species. Without wanting to be bound to a theory, the inventors consider that this is of special interest when a skilled artisan is performing regenerative medicine.

In certain embodiments, the nucleic acids and the nucleic acid vectors encompassed by the instant invention may be employed to engineer animal or plant models, e.g. animal models for preclinical studies, bearing in mind the fundamental ethical principles.

Another aspect of the invention concerns a nucleic acid for the controlled expression of a nucleic acid encoding a pro-apoptotic protein, as defined herein, for use as an active agent for adoptive cell transfer.

Methods

The methods disclosed herein may be achieved in vitro, in vivo or ex vivo.

Another aspect of the present invention concerns a method for inducing apoptosis into at least one target cell comprising at least the step of administering to an individual in need thereof of the nucleic acid for the controlled expression of a nucleic acid encoding a pro-apoptotic protein or the nucleic acid vector, as defined herein.

In one aspect, the invention concerns a method for treating and/or preventing a tumor comprising at least the step of administering to an individual in need thereof of the nucleic acid for the controlled expression of a nucleic acid encoding a pro-apoptotic protein or the nucleic acid vector, as defined herein.

In some embodiments, the methods above further comprise a step of providing the individual with a diet deficient in at least one essential amino acid, in particular an amino acid selected in a group comprising histidine (His, H), isoleucine (Ile, I), leucine (Leu, L), Lysine (Lys, K), methionine (Met, M), phenylalanine (Phe, F), threonine (Thr, T), tryptophane (Trp, W) and valine (Val, V).

In certain embodiments, the methods above alternatively comprise a step of administering a compound known to activate the AARE nucleic acid comprised in the regulatory polynucleotide, in particular a compound selected in a group comprising halofuginone, tunicamycin, and the like. In some embodiments, nucleic acid for the controlled expression of a nucleic acid encoding a pro-apoptotic protein or the nucleic acid vector may be formulated as a pharmaceutical composition, as described above.

In some embodiments, the pharmaceutical composition may be administered to an individual in need thereof by any route, i.e. by an oral administration, a topical administration or a parenteral administration, e.g., by injection, including a sub-cutaneous administration, a venous administration, an arterial administration, in intra-muscular administration, an intra-ocular administration, and an intra-auricular administration.

Other modes of administration employ pulmonary formulations, suppositories, and transdermal applications.

In some embodiments, an oral formulation according to the invention includes usual excipients, such as, for example, pharmaceutical grades of mannitol, lactose, starch, magnesium stearate, sodium saccharine, cellulose, magnesium carbonate, and the like.

In some embodiments, an effective amount of said compound is administered to said individual in need thereof.

Within the scope of the instant invention, an "effective amount" refers to the amount of said compound that alone stimulates the desired outcome, i.e. alleviates or eradicates the symptoms of the encompassed disease, in particular a cancer.

It is within the common knowledge of a skilled artisan to determine the effective amount of a nucleic acid for the controlled expression of a nucleic acid encoding a pro-apoptotic protein, or a nucleic acid vector or a delivery particle in order to observe the desired outcome.

Within the scope of the instant invention, the effective amount of the compound to be administered may be determined by a physician or an authorized person skilled in the art and can be suitably adapted within the time course of the treatment.

In certain embodiments, the effective amount to be administered may depend upon a variety of parameters, including the material selected for administration, whether the administration is in single or multiple doses, and the individual's parameters including age, physical conditions, size, weight, gender, and the severity of the disease to be treated.

Kit

In a further aspect, the invention concerns a kit for treating and/or preventing a tumor comprising:
a pharmaceutical composition, as defined herein, and
an anti-tumor compound.

In some embodiments, the anti-tumor compound may be selected by a skilled in the art from the compounds commonly employed in chemotherapy.

In certain embodiments, the anti-tumor compound may be selected in a group comprising an alkylating agent, a purine analogue, a pyrimidine analogue, an anthracycline, bleomycin, mytomycin, an inhibitor of topo-isomerase 1, an inhibitor of topo-isomerase 2, a taxan, a monoclonal antibody, a cytokine, an inhibitor of a protein kinase, and the like.

EXAMPLES

1/METHODS

1.1/Ethics Statement

The experimental data obtained herein are in accordance with INRA guidelines in compliance with European animal welfare regulation. Mice maintenance and all experiments have been approved by our institutional-animal care and use committee, in conformance with French and European Union laws (permission to experiment on mice B63-150, local ethic committee CEMEA CE10-13, animal facilities agreement C6334514, GMO agreement 4756CA-I).

1.2/Animals and Experimental Diets

C57Bl/6 transgenic mice expressing the luciferase gene under the control of AARE were engineered in our lab as described in Chaveroux et al. (Science signaling; 2015, 8(374):rs5). Fisher rats and BalB/C and C57Bl/6 mice were housed in an animal facility at INRA. Nude mice were purchased from Janvier labs (SM-NU-6S-M). For each experiment, six 6-week-old males per group were used. Animals were excluded from the study if they died during the period of time between intratumoral or tissular delivery of lentivirus and feeding protocols. Examiners were not blinded with respect to diet administration and treatments. Animals had ad libitum access to food and water at all times, unless otherwise indicated. Animals were individually housed in plastic cages and subjected to a 12 hours light/dark cycle at a temperature of 22° C., in a pathogen-free environment. Nutritional experiments were performed as previously in Maurin. et al. (Cell Metab, 2005, 1, 273-277).

In general terms, their design should be in compliance with the contingency related to working with rodents, taking into account that rodents constantly nibble and are coprophagous. Thus, before subjecting mice to amino acid-deprived meal, an overnight fasting period is essential, while ensuring that newly cleaned cages are provided to the animals during this period. In doing so, animals are starved and hungry when the meal is provided and will readily eat the nutritional diet. Food intake was controlled at each experiment. If necessary, force-feeding could also be an option but should be performed under conditions that are not stressful to animals. Experimental diets were manufactured in the INRA diets core facility (Unité de Préparation des Aliments Expérimentaux, INRA).

1.3/In Vivo Lentiviral Transduction and Hydrodynamic Injection Procedures

Pancreatic injections were conducted as follow: 6-week-old males C57Bl/6 mice were anesthetized with isoflurane and a laparotomy through midline incision was made. The lentiviral vector solution containing $2 \times 10^7$ particles was administrated into the splenic vein. Ten days after injection, 16-h fasted mice were fed a control or a diet devoid of isoleucine for 6 hours. At the end of the experiment, whole body and excised pancreas bioluminescence were measured by using a bioluminescence imaging system (IVIS spectrum, PerkinElmer).

Hippocampal administration of lentiviral particles was performed in 6-week-old males 344 rats (6 animals per group). Animals were anesthetized with isoflurane and placed in a stereotaxic frame. Before injections, lentiviral vectors were diluted with sterile PBS to achieve a titre of $10 \times 10^9$. Viral preparation in 2-µL volume was injected unilaterally into the dentate gyrus region of the hippocampus. The preparation was injected with a speed of 0.5 µL/min over a period of 4 min by using a Hamilton 5-µL syringe and a 27 G syringe.

Hydrodynamic injections were prepared by diluting 50 µg of pGL3-2XAARE TRB3-Tk-LUC plasmid in a saline physiological buffer corresponding to 10% body volume of the mouse and were administrated over a 5-sec period in to the tail vein of 6-week-old males BalB/C mice (6 animals per group). Twenty-four hours after injection, 16-h fasted mice were fed a control or a diet devoid of isoleucine for 6 hours. At the end of the experiment, whole body and excised livers bioluminescence were measured by using a bioluminescence imaging system (IVIS spectrum, PerkinElmer).

For in vivo bioluminescence experiments, after gene transfer methods, basal light emission was assessed through IVIS spectrum measurements. Mice were ranked respective to the luciferase activity and distributed into the experimental groups to insure equal average bioluminescence activity between the different groups.

1.4/In Vivo Tumor Xenograft Model

Tumors were obtained by injection of $2 \times 10^6$ Gli36-luc cells suspended in 200 µL, of DMEM into the left flank region. After a 1-week period for xenografts implantation, mice were ranked according to light emission of the tumors and then distributed into the experimental groups to insure equal average tumors volumes between the groups. Tumors were then injected with $10^9$ lentiviral particles and subjected to the indicated nutritional conditions. After a 1-week period for xenografts implantation, tumors were injected with $10^9$ lentiviral particles and subjected to the indicated nutritional conditions. The sizes of the resultant tumors were measured weekly with a bioluminescence imaging system (IVIS spectrum, Perkin-Elmer). At endpoint, mice were sacrificed and the tumors were harvested surgically, weighted, photographed and flash-frozen for subsequent protein analysis.

1.5/Plasma Amino Acid Analysis

Blood samples were drawn from the aorta of anesthetized mice. Plasma amino acids were purified, i.e., 100 µL of plasma was added to 30 µL of sulfosalicylic acid solution (1 mol/L in ethanol with 0.5 mol/L thiodiglycol) which was previously evaporated. We added norleucine as an internal standard to evaluate sample treatment efficiency, which was then used to correct the raw values. Amino acid concentrations were determined using an L8900 amino acid analyzer (ScienceTec, Courtaboeuf, France) with BTC 2410 resin (Hitachi Chemical).

1.6/Body Measurements

Fat and lean masses were determined by placing restrained individual mice into the mouse EchoMRI-100 instrument (Echo Medical Systems LLC). For muscle wasting assessment, after 24 days of experiment, the gastrocnemius, soleus and tibialis anterior hind limb skeletal muscles were weighted. Results from mice fed EAA-deficient diets were reported to the control group data and expressed as a percentage.

1.7/Cell Culture and Lentiviral Transduction

Mouse embryonic fibroblasts (MEF), HeLa and Gli36-luc cells were cultured at 37° C. in Dulbecco's modified Eagle's medium F12 (DMEM F12) (Sigma) containing 10% fetal bovine serum. When indicated, DMEM F12 lacking leucine (DMEM F12 Base) (Sigma) was used. In all experiments involving amino acid starvation, 10% dialyzed calf serum was used. Gli36-Luc cells were a gift of Dr. Shah K. (Harvard Medical School, Boston, MA). GCN2−/− and PERK−/− MEFs were given by Drs D. Ron and H. Harding (Institute of Metabolic Science, Cambridge, UK). PKR−/− MEFs were from Dr John C Bell (Ottawa health research institute, Canada). KO MEFs were validated by PCR and Western Blot analyses and Gli36-Luc cells by luciferase assays. All the cell lines were *mycoplasma* free. Gli36-luc cells were transduced with either the LV-AARE-eGFP or LV-AARE-TRAIL vectors by using an MOI of 10, in the presence of polybrene (5 µg/mL). 48 hours after infections, cells were transferred to 10 cm dishes and maintained for experimental purposes.

1.8/Immunoblot Analysis and Antibodies

Western blots were performed as previously described in Maurin. et al. (Cell reports, 2014, 6, 438-444). Primary antibodies used were: anti-phospho-eIF2α (Abcam, ab32157), anti-ATF4 (Santa Cruz, sc-200), anti-Actin (Santa Cruz, sc-1616R), anti-cleaved PARP (Cell signaling tech., 5625), anti-TRAIL (Cell signaling tech., 3219).

1.9/Transient Transfection and Luciferase Assays

Cells were plated in 24 well plates and transfected by the calcium phosphate co-precipitation method, as described previously in Bruhat et al. (Mol Cell Biol, 2000, 20, 7192-7204). For all transfection experiments, a plasmid pCMV-βGAL was used as an internal control. Relative luciferase activity was given as the ratio of relative luciferase unit/relative β-Gal unit. All values are the means calculated from the results of three independent experiments (3 samples per group).

1.10/Plasmid and Lentivirus Constructions

2XAARE TRB3-Tk-LUC, 2XAARE CHOP-Tk-LUC and 2XAARE ATF3-Tk-LUC plasmids were constructed by inserting SacI-XhoI double-stranded oligonucleotides containing two copies of the different AARE sequence into the pcDNA3-TK-Luc plasmid. The 2XAARE TRB3-β-globin-LUC construct was obtained by replacing the TK minimal promoter sequence flanked by the Xho1 and HindIII restriction sites with a double-stranded sequence corresponding to the various AARE sequences. 2XAARE TRB3-Tk-eGFP and 2XAARE TRB3-Tk-TRAIL lentiviruses were obtained by synthesizing eGFP and the human TRAIL cDNA sequences (GeneCust) flanked by Nco1 and Xba1 restriction sites. DNA cassettes were then inserted in an HIV-INS vector containing two copies of the AAREs from the Trib3 gene. 2XAARE TRB3-Tk-eGFP and 2XAARE TRB3-Tk-TRAIL lentiviruses were produced in the Vectorology facility (ICM, Paris).

For ease of manipulation, the 2XAARE TRB3-Tk-TRAIL construction was first implemented in a pENTR plasmid, as described by SEQ ID NO: 8.

1.11/Cell Survival, Apoptosis and ELISA Assays

The viability of the cells was measured with the XTT cell viability kit (Cell signaling tech., 9095). Apoptosis was evaluated by flow cytometry analysis with the ANXA5/PE/7-AAD Apoptosis detection kit (BD Biosciences, 559763) following the manufacturer's instructions. Regarding ELISA assays, 16 h after treatment the media were collected and used for TRAIL protein determination with the Human TRAIL/TNFSF10 Quantikine ELISA kit (R&D systems, DTRL00).

1.12/Statistics

Each cellular experiment was repeated 3 times. All animal experimental groups were composed of 6 mice or rats. All statistical analyses were generated using GraphPad Prism 6 (GraphPad Software) and all data are expressed as means±SEM. For the comparison between two or more experimental groups, statistical significance was assessed via Student's t test or two-way ANOVA (followed by Bonferroni's post-hoc test adjusting the pair-wise comparison p value) with an alpha level of 0.05. *$p<0.05$, $p<0.01$ and *$p<0.001$.

2/RESULTS 2.1/Optimization and In Vivo Validation of a Heterologous System Controlling Transcription in Response to Amino Acid Limitation Based on previous results, a new gene expression system controlled by EAA availability was optimized. As previously reported, the expression of Trb3, Chop and Atf3 genes is up-regulated following activation of the GCN2-eIF2α-ATF4 pathway, and implicates the recruitment of ATF4 to specific AAREs to induce their expression (FIG. 1). These AAREs are present as a single copy of the core sequence within the Chop and Atf3 promoter, or as a repetition of three copies in the Trb3 promoter.

Different combinations of these AAREs fused with two minimal promoters (Thymidine Kinase and β-globin), using luciferase as a reporter gene, were tested in transfected Mouse Embryonic Fibroblasts (MEF). The highest responsiveness was obtained with two copies of the Trb3 AARE (6 repeats of the core sequence) associated with the TK promoter, yielding a 6-fold induction in response to leucine starvation with a low background level (not shown). The construct with the β-globin minimal promoter provided a similar induction level, with a corresponding background level 3-fold higher than with the TK promoter (not shown). Thus, all further experiments were carried out with two Trb3 AARE associated with the TK minimal promoter. This construct was designated the AARE-Driven Expression System (FIG. 2).

Finally, the maintenance of the inducibility of this construct by amino acid starvation was validated, when stably integrated in mouse (MEF) or human (HeLa) cells (not shown). Other than GCN2, eIF2α can be phosphorylated in mammalian tissues by three other kinases: PKR (activated by dsRNA and cytokines), PERK (activated by endoplasmic reticulum stress), or HRI (activated by heme deficiency). HRI is expressed in an erythroid cell-specific manner; therefore the attention was focused on the role of the ubiquitously expressed kinases GCN2, PKR and PERK. In response to leucine starvation, luciferase induction was completely abolished in GCN2−/− cells, whereas no effect was observed in PERK−/− and PKR−/− cells, demonstrating that transgene regulation is strictly dependent on GCN2 expression (not shown). Next, we tested in vitro induction of luciferase expression with respect to the concentration of leucine. The induction of reporter gene expression is inversely dependent on leucine concentration (not shown). Most notably, in this in vitro experiment, the leucine concentration that triggers transcription activation is similar to that obtained in mammals after consumption of a leucine-deficient diet, suggesting that it may also be equally efficient in vivo.

Considering that organisms rapidly absorb dietary free amino acids, a synthetic diet was prepared, in which the protein fraction is replaced by a mixture of free amino acids. In this condition, when the diet is lacking one EAA the level of this EAA in the blood should rapidly decrease. To translate the concept of this gene regulation system to animals, we first tested the effect of leucine-deficient diet on post-prandial blood leucine content. FIG. 3 shows that the blood leucine level was increased during the post-prandial period after consumption of a control meal. In sharp contrast, leucinemia dramatically decreased as early as 30 min after consumption of a diet devoid of leucine.

In vivo validation of the AARE-driven expression system was further assessed by taking advantage of an AARE-driven luciferase mouse model previously engineered Chaveroux et al. (Science signaling, 2015, 8(374):rs5). Consumption of a leucine-free diet resulted in a significant increase in bioluminescence in the abdominal cavity as soon as 3 h and was maintained for at least 12 h (FIG. 4). A fasting period of 16-24 h had no effect on transgene expression (FIG. 5). Previous work showed that the GCN2-eIF2α-ATF4 pathway is rapidly activated in vivo following consumption of a leucine-devoid diet. For example, the hepatic mRNA encoding Trb3 is significantly induced one hour following the beginning of a leucine-free meal. The delay to obtain measurable bioluminescence is due to the necessity to accumulate enough luciferase. As anticipated from previous in-vitro results this experiment provided a clear indication that the AARE-Driven Expression System functions in vivo as well.

2.2/Determination of the Optimal Nutritional Induction of the AARE-Driven Expression System In mammals, 9 EAA must be supplied in the diet and a lack of any one of them represents a potential inducer of the AARE-Driven Expression System. The effect of diets independently depleted of each of the 9 EAA was compared with respect to the level of luciferase expression driven by AARE. First, it was ascertained that the blood concentration of the lacking EAA drops significantly following diet consumption. The extent of the decrease varies from one amino acid to another (not shown). The induction ratio of luciferase activity was measured in AARE-driven luciferase mice by in-vivo bioluminescence imaging 6 h after switching animals to the specific diet. The induction ratio varied from 5 to over 50 in the case of isoleucine or tryptophan starvation. As expected, no luciferase induction was observed in fasted mice or in mice fed on a diet deprived of a non-essential amino acid such as alanine. These results highlight the flexibility of the AARE-Driven Expression System, in which each individual EAA can act as a potential inducer.

2.3/A "Nutrition-Based" Protocol for Long-Term Transgene Expression

Gene therapy may require long-term expression of the transgene. In considering that long-term EAA deprivation is not physiologically relevant, the ability of maintaining a long-term expression of the transgene was tested by taking advantage of the flexibility the AARE-Driven Expression System. To that end, pulses of amino acid deprived diet swapping each of the lacking EAA were performed. In this paradigm, AARE-driven luciferase mice were subjected for 6 days to a nutritional cycle as described in FIG. 6. Monitoring abdominal bioluminescence was performed every day (FIG. 7). The quantification of bioluminescence clearly showed that transgene expression returned to a near-basal level 24 h after the dietary challenges. Re-induction followed similar kinetics with maximal levels depending on the lacking AA. Feeding cycles of an EAA-deficient diet have no effects on protein metabolism, provided that the amino acid differs from one cycle to the other. Body weight, percentage of lean and fat mass and weight of muscle was monitored in animals that have been subjected for 24 days to the above cycling nutritional protocol (4 nutritional cycles as shown FIG. 8). As illustrated in FIG. 9-12, none of these physiological parameters was modified relative to control.

2.4/The Nutrition-Based Regulatory System is Effective in the Context of In Vivo Gene Transfer The capacity of nutrition to regulate the AARE-Driven Expression System in gene transfer experimental settings was then investigated, by targeting various tissues relevant for gene therapy. Although the GCN2-eIF2α-ATF4 pathway is ubiquitous, certain organs are more sensitive than others to an EAA-free diet. Data from transgenic mice fed an EAA-deficient diet showed that this pathway was functional in the brain and many metabolic organs including the liver and the pancreas (not shown). Similarly to the previous experiments based on transgenic mice, animals were fed a nutritional protocol that includes overnight starvation, followed by feeding for 6 hours on a isoleucine-deficient diet.

In a series of experiments, first hydrodynamic injection of plasmid carrying luciferase driven by AAREs was explored into the tail vein of Balb/C mice allowing hepatic transfection. Bioluminescence in the abdominal area and in the collected livers was dramatically induced in response to a 6-h dietary isoleucine starvation compared to the control diet (FIG. 13). Luciferase assay of hepatic protein extracts confirmed this increase of luciferase activity (FIG. 14).

In a second set of experiment, pancreatic tissues were transduced with a lentiviral vector carrying luciferase driven by AAREs. A clear induction of luminescence was observed in the pancreas in response to the inducer diet, which was confirmed by measuring luciferase activity in protein extracts (FIGS. 15 and 16). No signal was detected in other parts of the mice. Finally, to test the regulation of the AARE-Driven Expression System in the brain, lentiviral injection of the AARE-Driven Luc expression system was performed in the hippocampus of rats, a cerebral region that is easily accessible by stereotaxic injection. The left hippocampus received lentiviral particles containing the AARE-Luc sequence, whereas the right received particles without AARE sequences. At the completion of the nutritional protocol, luciferase activity was measured in brain extracts. As shown in FIG. 17, brain extracts of the left hippocampus containing the vector harboring the AARE-Driven Luc expression system exhibited increased luciferase activity, whereas the right hippocampus and the non-injected area of the left hippocampus expressed a background activity.

In the context of these in vivo studies, it was observed that the AARE-Driven Expression System can be pharmacologically induced in liver and in pancreas following intraperitoneal injection of halofuginone, a pharmacological activator of GCN2 that mimics amino-acid starvation by inhibiting prolyl-tRNA synthetase 18 (not shown). Pharmacological activation of GCN2 could provide an alternative to the nutritional protocol. However, a careful assessment of the specificity, pharmacokinetics and potential adverse effects of halofuginone is being awaited.

2.5/Application of the "Nutrition-Based" Protocol to Regulate the Expression of a Hazardous Therapeutic Factor In some instances, the level of therapeutic factors may need to be tightly regulated according to the need of the patient and/or its expression abrogated in case of undesirable toxic effects. TRAIL was chosen as a gene of interest. TRAIL is a secreted cytokine that acts in a paracrine manner by binding to specific death receptors to initiate apoptosis. TRAIL has been intensely investigated, particularly in glioblastoma cells. It has a short biological half-life (30 min) and is rapidly cleared from the body after systemic administration. However, prolonged exposure of normal human cells to TRAIL could still be toxic.

In that context, the long-term "nutrition-based" protocol may represent a suitable solution to regulation of TRAIL expression. Human Gli36-luciferase cells were used as a model for glioblastoma cells. These cells, which constitutively expressed luciferase, were transduced with the AARE-Driven TRAIL Expression System. First, it was ascertained that TRAIL protein expression was induced in response to leucine starvation, secreted into the culture medium, had a paracrine effect on surrounding cells and triggered apoptosis (not shown).

Finally, we tested the effects of TRAIL expression on Gli36-luciferase glioblastoma xenografts in nude mice. The lentiviral vector was directly injected into the tumor (1 week following cells implantation) and the long-term "nutrition-based" protocol described above was applied for 2 weeks. Tumors development was assessed by bioluminescence imaging. Remarkably, TRAIL expression prevented tumor growth with no apparent toxicity at a gross level (−EAA group), whereas similar animals fed on a control diet showed no inhibition (Ctrl group) (FIGS. 18 and 19). Immunoblot analysis of protein from tumors showed that only mice from the −EAA group displayed an elevation of the apoptosis marker cleaved-PARP, indicating that an apoptotic process occurred in these cells and not in the counterpart controls (FIGS. 20 and 21).

Importantly, TRAIL protein was detected solely in tumors from the −EAA group, after 6 h of the −Ile diet period. As expected, the nutritional protocol by itself had no effects on tumor growth (not shown). Collectively, these findings validate the capacity of the AARE-Driven Expression system to generate pulses of transgene expression, thereby allowing long-term/intermittent gene therapy treatments.

3/DISCUSSION

The temporal regulation of therapeutic gene expression has long been awaited to broaden the clinical utility of gene therapy. It is shown herein how a regulatory system, initially discovered in the context of basic studies pertaining to the physiology of nutritional deprivation, provides a remarkably simple, highly specific, reliable and robust means for controlling the expression of exogenous transgenes, and exhibits the desirable properties for translation from the laboratory to clinical practice.

The development of this nutrition-based regulatory system takes advantage of the adaptive GCN2-eIF2α-ATF4 signal transduction pathway that senses amino acid deficiency. This pathway, which is conserved from yeast to human, is triggered when omnivorous animals are confronted with food restricted in one EAA, a situation that may occur frequently in the wild if only a single plant protein source is accessible.

The activation of the GCN2-eIF2α-ATF4 pathway occurs exclusively in response to the consumption of an EAA unbalanced diet and is engaged in no other human nutritional conditions. Physiological conditions, such as fasting, do not affect the amino acids blood concentration to such an extent that it would trigger the GCN2 pathway. In response to a prolonged fasting, the blood concentration of all amino acids would be maintained through a compensation mechanism involving increased proteolysis in liver and then in muscle.

The GCN2-eIF2α-ATF4 pathway has been found in numerous tissues such as liver, pancreas and in different parts of the brain, revealing thereby the large potential applicability of the AARE-driven expression system to numerous diseases. It is unique and exhibits no inherent toxicity, as it is not based on an exogenous ligand-inducible system relying on non-human/viral transcriptions factors/regulatory proteins, which could generate immune responses. Moreover, it obviates the need of pharmacological inducers, which could generate toxic effects, especially for long-term treatments.

The nutrient-based regulatory system offers a robust and flexible means to precisely tune the expression of a desired gene since the inducer diets are composed of free amino acids that are easily absorbed, thereby leading to a rapid EAA blood drop kinetics and triggering of therapeutic transgene. The level of expression of a given transgene will depend upon the specific EAA lacking in the diet. A diet composed of free amino acid taken by a patient, in the morning, is not anticipated to be a challenge for the patients. Using ready-to-eat diet package would be similar to taking food complements. In this clinical context, it is also particularly worth noting that a medical formula of leucine free diet, available on the market and validated in Maple syrup urine disease (MSUD), could be readily used in conjunction with the AARE system. In addition, novel formula tailored to the individual needs and tastes of the patient can be developed. Following the induction period, patients could after a few hours resume eating normal diet. When required, sustained expression of the transgene can be obtained by alternating diets, every day or every few days.

Timely exogenous regulation of transgene expression appears to be particularly suitable in the context of pharmacological gene therapies as opposed to gene replacement/surgery. The latter strategy allows the replacement of a defective gene by a bona fide functional counterpart, thereby obviating the need for exogenous regulation. In contrast, pharmacological gene therapies, which are similar to conventional pharmacological treatments, may require long-term/intermittent regulation of the transgene expression. Pertinent situations are represented by tropic factors that are receiving considerable attention in the context of neurodegenerative disorders. In Particular, the glial cell line-derived neurotrophic factor (GDNF), has been shown to be essential for the survival of dopaminergic neurons in the adult brain, and gene therapies approaches are being evaluated for Parkinson's disease.

The dynamics of a given regulatory system is a key feature in addressing the pharmacological properties of a given medication supplied through gene transfer. To be clinically relevant a gene regulatory system should be regulated over a wide dose range of the inducer, within a safe dose of the vector, and exhibit a low level of background expression. In this regard, the study of the pro-apoptotic TRAIL cytokine described in the Results section provided a direct and quantitative comparison between transgene expression and the resulting physiological/clinical effect.

Specifically, the level of TRAIL expressed in the induced tumor was, in the absence of dietary isoleucine, estimated to be over hundred fold more intense than the faint signal obtained under control conditions. Remarkably, TRAIL expression prevented tumor growth with no apparent toxicity at the gross level, whereas animals fed on a control diet showed no tumor inhibition. Such a high ratio of induction associated with the nutritional protocol offers great flexibility in adapting transgene expression levels to optimal therapeutic levels, and to abrogate the background activity when required. Thus, in the clinical setting, one should be in a position to generate efficient and safe doses of therapeutic molecule through the handling of the (i) dose of the therapeutic vector, (ii) strength of the minimal promoter driving the therapeutic transgene, (iii) (de)stabilization of the corresponding RNA, (iv) selection of the EEA-deprived diet, that would satisfy all efficacy and safety concerns.

The AARE system may, in particular situations, act as an endogenously controlled system in view of the fact that the eIF2α-ATF4 signalling pathway is part of one of the three branches of the ER stress response. Thus, following delivery of the vector strictly within diseased tissues, AARE-dependent transcription can become internally activated in situations such as certain tumors or certain brain areas of patients suffering from Alzheimer's or Parkinson's disease. In these instances, the expression of a therapeutic gene could be triggered endogenously, without resorting to an EAA-deficient diet. Alternatively, when the therapeutic factor is a secreted protein with paracrine effect, the therapeutic effect may be obtained by injection of the vector into neighbouring healthy tissue followed by dietary induction.

Lastly, the nutrition-based regulatory system was shown to be effective in the context of a vector backbone, such as that of the lentiviral vector which transduces many types of cells efficiently and is among the most promising viral vectors currently used in gene therapy trials. This finding calls for the testing of other vectors for their capacities to express the AARE system, which may further exemplify the flexibility and potential of the nutrition-regulated system. Clearly, the AARE system highlights a new concept in the field of gene therapy, that synthetic diets can enable a tight and robust temporal control of therapeutic transgene expression, thereby unlocking a frequent hurdle in the translation of gene therapy protocols to clinical fruition.

NUCLEIC SEQUENCES USED IN THE INVENTION

The Table 1 below discloses the nucleic acid sequences used herein:

| SEQ ID No: | Sequences | Comments |
|---|---|---|
| 1 | CGGTTTGCATCACCCG | AARE sequence from the TRIB3 gene |

| SEQ ID No: | Sequences | Comments |
|---|---|---|
| 2 | AACATTGCATCATCCC | AARE sequence from the CHOP gene |
| 3 | GAAGTTTCATCATGCC | AARE sequence from the ASNS gene |
| 4 | AGCGTTGCATCACCCC | AARE sequence from the ATF3 gene |
| 5 | GATATTGCATCAGTTT | AARE sequence from the SNAT2 gene |

Regulatory Polypeptide Comprising the Thymidine Kinase (Tk) Minimal Promoter and Six Copies of the AARE Nucleic Acid Sequence from the TRIB3 Gene: SEQ ID NO: 6

GGTACCGATTAGCTCCGGTTTGCATCACCCGGACCGGGGGATTAGCTCCG
GTTTGCATCACCCGGACCGGGGGATTAGCTCCGGTTTGCATCACCCGGAC
CGGGGGCCGGGCGCGTGCTAGCGATTAGCTCCGGTTTGCATCACCCGGAC
CGGGGGATTAGCTCCGGTTTGCATCACCCGGACCGGGGGATTAGCTCCGG
TTTGCATCACCCGGACCGGGGACTCGAGGTCCACTTCGCATATTAAGGTG
ACGCGTGTGGCCTCGAACACCGAGCGACCCTGCAGCGACCCGCTTAACAG
CGTCAACAGCGTGCCGC cDNA of TRAIL Protein: SEQ ID NO: 7

ATGGCTATGATGGAGGTCCAGGGGGACCCAGCCTGGGACAGACCTGCGT
GCTGATCGTGATCTTCACAGTGCTCCTGCAGTCTCTCTGTGTGGCTGTAA
CTTACGTGTACTTTACCAACGAGCTGAAGCAGATGCAGGACAAGTACTCC
AAAAGTGGCATTGCTTGTTTCTTAAAAGAAGATGACAGTTATTGGGACCC
CAATGACGAAGAGTATGAACAGCCCCTGCTGGCAAGTCAAGTGGCAAC
TCCGTCAGCTCGTTAGAAAGATGATTTTGAGAACCTCTGAGGAAACCATT
TCTACAGTTCAAGAAAAGCAACAAAATATTTCTCCCCTAGTGAGAGAAAG
AGGTCCTCAGAGAGTAGCAGCTCACATAACTGGGACCAGAGGAAGAAGCA
ACACATTGTCTTCTCCAAACTCCAAGAATGAAAAGGCTCTGGGCCGCAAA
ATAAACTCCTGGGAATCATCAAGGAGTGGGCATTCATTCCTGAGCAACTT
GCACTTGAGGAATGGTGAACTGGTCATCCATGAAAAGGGTTTTACTACA
TCTATTCCCAAACATACTTTCGATTTCAGGAGGAAATAAAAGAAAACACA
AAGAACGACAAACAAATGGTCCAATATATTTACAAATACACAAGTTATCC
TGACCCTATATTGTTGATGAAAAGTGCTAGAAATAGTTGTTGGTCTAAAG
ATGCAGAATATGGACTCTATTCCATCTATCAAGGGGAATATTTGAGCTT
AAGGAAAATGACAGAATTTTTGTTTCTGTAACAAATGAGCACTTGATAGA
CATGGACCATGAAGCCAGTTTTTTTGGGGCCTTTTTAGTTGGCTAAACCG
GTGCTAGCTCTAGA

Plasmid pENTR Comprising Six Copies of the AARE Nucleic Acid from Trib3 Gene Sequence, Tk Minimal Promoter and the cDNA Encoding for TRAIL Protein: SEQ ID NO: 8

CACCGGTACCGATTAGCTCCGGTTTGCATCACCCGGACCGGGGGATTAGC
TCCGGTTTGCATCACCCGGACCGGGGGATTAGCTCCGGTTTGCATCACCC
GGACCGGGGCCGGGCGCGTGCTAGCGATTAGCTCCGGTTTGCATCACCC
GGACCGGGGGATTAGCTCCGGTTTGCATCACCCGGACCGGGGGATTAGCT
CCGGTTTGCATCACCCGGACCGGGGACTCGAGGTCCACTTCGCATATTAA
GGTGACGCGTGTGGCCTCGAACACCGAGCGACCCTGCAGCGACCCGCTTA
ACAGCGTCAACAGCGTGCCGCAAGCTTGAATTCTGATCAGCATTCCGGTA
CTGTTGGAAAGCCACCATGGCTATGATGGAGGTCCAGGGGGACCCAGCC
TGGGACAGACCTGCGTGCTGATCGTGATCTTCACAGTGCTCCTGCAGTCT
CTCTGTGTGGCTGTAACTTACGTGTACTTTACCAACGAGCTGAAGCAGAT
GCAGGACAAGTACTCCAAAAGTGGCATTGCTTGTTTCTTAAAAGAAGATG
ACAGTTATTGGGACCCCAATGACGAAGAGTATGAACAGCCCCTGCTGG
CAAGTCAAGTGGCAACTCCGTCAGCTCGTTAGAAAGATGATTTTGAGAAC
CTCTGAGGAAACCATTTCTACAGTTCAAGAAAAGCAACAAAATATTTCTC
CCCTAGTGAGAGAAAGAGGTCCTCAGAGAGTAGCAGCTCACATAACTGGG
ACCAGAGGAAGAAGCAACACATTGTCTTCTCCAAACTCCAAGAATGAAAA
GGCTCTGGGCCGCAAAATAAACTCCTGGGAATCATCAAGGAGTGGGCATT
CATTCCTGAGCAACTTGCACTTGAGGAATGGTGAACTGGTCATCCATGAA
AAAGGGTTTTACTACATCTATTCCCAAACATACTTTCGATTTCAGGAGGA
AATAAAAGAAAACACAAAGAACGACAAACAAATGGTCCAATATATTTACA
AATACACAAGTTATCCTGACCCTATATTGTTGATGAAAAGTGCTAGAAAT
AGTTGTTGGTCTAAAGATGCAGAATATGGACTCTATTCCATCTATCAAGG
GGGAATATTTGAGCTTAAGGAAAATGACAGAATTTTTGTTTCTGTAACAA
ATGAGCACTTGATAGACATGGACCATGAAGCCAGTTTTTTTGGGGCCTTT
TTAGTTGGCTAAACCGGTGCTAGCTCTAGAAAGGGTGGGCGCGCCGACCC
AGCTTTCTTGTACAAAGTTGGCATTATAAGAAAGCATTGCTTATCAATTT
GTTGCAACGAACAGGTCACTATCAGTCAAAATAAAATCATTATTTGCCAT
CCAGCTGATATCCCCTATAGTGAGTCGTATTACATGGTCATAGCTGTTTC
CTGGCAGCTCTGGCCCGTGTCTCAAAATCTCTGATGTTACATTGCACAAG
ATAAAAATATATCATCATGAACAATAAAACTGTCTGCTTACATAAACAGT
AATACAAGGGGTGTTATGAGCCATATTCAACGGGAAACGTCGAGGCCGCG
ATTAAATTCCAACATGGATGCTGATTTATATGGGTATAAATGGGCTCGCG
ATAATGTCGGGCAATCAGGTGCGACAATCTATCGCTTGTATGGGAAGCCC

-continued

```
GATGCGCCAGAGTTGTTTCTGAAACATGGCAAAGGTAGCGTTGCCAATGA
TGTTACAGATGAGATGGTCAGACTAAACTGGCTGACGGAATTTATGCCTC
TTCCGACCATCAAGCATTTTATCCGTACTCCTGATGATGCATGGTTACTC
ACCACTGCGATCCCCGGAAAAACAGCATTCCAGGTATTAGAAGAATATCC
TGATTCAGGTGAAAATATTGTTGATGCGCTGGCAGTGTTCCTGCGCCGGT
TGCATTCGATTCCTGTTTGTAATTGTCCTTTTAACAGCGATCGCGTATTT
CGTCTCGCTCAGGCGCAATCACGAATGAATAACGGTTTGGTTGATGCGAG
TGATTTTGATGACGAGCGTAATGGCTGGCCTGTTGAACAAGTCTGGAAAG
AAATGCATAAACTTTTGCCATTCTCACCGGATTCAGTCGTCACTCATGGT
GATTTCTCACTTGATAACCTTATTTTTGACGAGGGGAAATTAATAGGTTG
TATTGATGTTGGACGAGTCGGAATCGCAGACCGATACCAGGATCTTGCCA
TCCTATGGAACTGCCTCGGTGAGTTTTCTCCTTCATTACAGAAACGGCTT
TTTCAAAAATATGGTATTGATAATCCTGATATGAATAAATTGCAGTTTCA
TTTGATGCTCGATGAGTTTTTCTAATCAGAATTGGTTAATTGGTTGTAAC
ACTGGCAGAGCATTACGCTGACTTGACGGGACGGCGCAAGCTCATGACCA
AAATCCCTTAACGTGAGTTACGCGTCGTTCCACTGAGCGTCAGACCCCGT
AGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGC
GCAGATACCAAATACTGTCCTTCTAGTGTAGCCGTAGTTAGGCCACCACT
TCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTC
```

-continued

```
AAGACGATAGTTACCGGATAAGGCGCAGCGGTCGGGCTGAACGGGGGGTT
CGTGCACACAGCCCAGCTTGGAGCGAACGACCTACACCGAACTGAGATAC
CTACAGCGTGAGCATTGAGAAAGCGCCACGCTTCCCGAAGGGAGAAAGGC
GGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGC
CACCTCTGACTTGAGCGTCGATTTTTGTGATGCTCGTCAGGGGGCGGAG
CCTATGGAAAAACGCCAGCAACGCGGCCTTTTTACGGTTCCTGGCCTTTT
GCTGGCCTTTTGCTCACATGTTCTTTCCTGCGTTATCCCCTGATTCTGTG
GATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAA
TACGCAAACCGCCTCTCCCCGCGCGTTGGCCGATTCATTAATGCAGCTGG
CACGACAGGTTTCCCGACTGGAAAGCGGGCAGTGAGCGCAACGCAATTAA
TACGCGTACCGCTAGCCAGGAAGAGTTTGTAGAAACGCAAAAAGGCCATC
CGTCAGGATGGCCTTCTGCTTAGTTTGATGCCTGGCAGTTTATGGCGGGC
GTCCTGCCCGCCACCCTCCGGGCCGTTGCTTCACAACGTTCAAATCCGCT
CCCGGCGGATTTGTCCTACTCAGGAGAGCGTTCACCGACAAACAACAGAT
AAAACGAAAGGCCCAGTCTTCCGACTGAGCCTTTCGTTTTATTTGATGCC
TGGCAGTTCCCTACTCTCGCGTTAACGCTAGCATGGATGTTTTCCCAGTC
ACGACGTTGTAAAACGACGGCCAGTCTTAAGCTCGGGCCCCAAATAATGA
TTTTATTTTGACTGATAGTGACCTGTTCGTTGCAACAAATTGATGAGCAA
TGCTTTTTTATAATGCCAACTTTGTACAAAAAAGCAGGCTCCGCGGCCGC
CCCCTT
```

The invention claimed is:

1. A method for eliminating infused cells which contain a nucleic acid comprising:
   a regulatory polynucleotide comprising a minimal promoter and at least one AARE (amino acid response element) nucleic acid, the regulatory polynucleotide being activated in a human individual upon consumption of a diet deficient in at least one essential amino acid; and
   a suicide safety gene selected from the group consisting of: BCL2 modifying factor, Apoptosis inducer NBK, Apoptotic protease-activating factor 1 (APAF1, CED4), BAX, Endophilin B1, FADD, CRADD, FAS, Modulator of apoptosis 1, SMAC, Endonuclease G, HRK, Serine protease HTRA2, p53, NOXA, RIPK1, Bcl2 binding component 3, PMAIP1, Tumor necrosis factor receptor superfamily member 10A Precursor (Death receptor 4), caspase 1, caspase 3, caspase 7, caspase 8, and caspase 9, the product of which is associated with the killing of cells, said suicide safety gene being placed under the control of the regulatory polynucleotide, the method comprising:
   a) administering the infused cells to a human individual in need of cancer treatment or regenerative medicine, and then
   b) eliminating the infused cells by inducing programmed cellular death into at least one of the infused cells by submitting the human individual to a diet deficient in at least one essential amino acid.

2. The method according to claim 1, wherein in the nucleic acid, the amino acid response element (AARE) nucleic acid is a nucleic acid of a sequence selected from the group consisting of SEQ ID No: 1, SEQ ID No: 2, SEQ ID No: 3, SEQ ID No: 4 and SEQ ID No: 5.

3. The method according to claim 1, wherein in the nucleic acid, the regulatory polynucleotide comprises at least two AARE nucleic acids.

4. The method according to claim 1, wherein the nucleic acid comprises a suicide gene encoding a protein performing a suicide task, which protein is selected from the group consisting of caspase 1, caspase 3, caspase 7, caspase 8 and caspase 9.

5. The method according to claim 4, wherein the protein performing a suicide task is caspase 9.

6. The method according to claim 1, wherein the nucleic acid is comprised in a nucleic acid vector for the controlled expression of a suicide safety gene.

7. The method according to claim 1, wherein the nucleic acid, or a nucleic acid vector comprising the nucleic acid, is comprised in a delivery particle.

8. The method according to claim 7, wherein the delivery particle comprises at its surface one or more ligands suitable for binding to a target receptor exposed at the membrane of a targeted cell.

9. The method according to claim 1, wherein the infused cells are selected from the group consisting of CAR T-cells and stem cells.

10. The method according to claim 1, wherein the infused cells are stem cells selected from the group consisting of hematopoietic stem cells and iPS cells.

* * * * *